US007569342B2

(12) United States Patent
Baker

(10) Patent No.: US 7,569,342 B2
(45) Date of Patent: *Aug. 4, 2009

(54) REMOVAL OF MOLECULAR ASSAY INTERFERENCES

(75) Inventor: Tony Baker, Sonora, CA (US)

(73) Assignee: Sierra Molecular Corp., Sonora, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/932,122

(22) Filed: Aug. 16, 2001

(65) Prior Publication Data

US 2002/0102580 A1    Aug. 1, 2002

Related U.S. Application Data

(63) Continuation-in-part of application No. 09/805,785, filed on Mar. 13, 2001, now abandoned, which is a continuation of application No. 09/185,402, filed on Nov. 3, 1998, now abandoned, which is a continuation-in-part of application No. 08/988,029, filed on Dec. 10, 1997, now abandoned.

(51) Int. Cl.
*C12Q 1/68* (2006.01)
*C12P 19/34* (2006.01)

(52) U.S. Cl. .................. 435/6; 435/91.2; 435/91.5; 435/91.52

(58) Field of Classification Search .............. 435/6, 435/91.1, 91.2; 424/529, 545; 536/23.1
See application file for complete search history.

(56) References Cited

U.S. PATENT DOCUMENTS

| 3,847,738 A | 11/1974 | Brake et al. ............. 195/1.8 |
| 4,040,785 A | 8/1977 | Kim et al. ............. 23/230 B |
| 4,703,008 A | 10/1987 | Lin ............. 435/240.2 |
| 4,741,446 A | 5/1988 | Miller ............. 215/247 |
| 4,812,310 A | 3/1989 | Sato et al. ............. 424/101 |

(Continued)

FOREIGN PATENT DOCUMENTS

DE    10031236    6/2000

(Continued)

OTHER PUBLICATIONS

Chung et al., Mol. Cells; pp. 108-111, 1996.*

(Continued)

*Primary Examiner*—Diana B Johannsen
(74) *Attorney, Agent, or Firm*—King & Spalding L.L.P.

(57) ABSTRACT

Methods and systems for removing masking agents from test samples, e.g., DNA-containing samples obtained from living subjects, when they are submitted for or subjected to molecular assays. The present invention allows molecular assays of nucleic acids in bodily fluids and excretions, such as urine, blood, blood serum, amniotic fluid, spinal fluid, conjunctival fluid, salivary fluid, vaginal fluid, stool, seminal fluid, and sweat to be carried out with greater sensitivity. The masking agents are suppressed by contacting a test sample with an amount of one or more divalent metal chelators and an amount of one or more chelator enhancing components. The amounts of the divalent metal chelator(s) and the chelator enhancing component(s) are selected such that interference of a masking agent on a molecular assay of a nucleic acid-containing test sample are suppressed, and upon contact with the divalent metal chelator(s)/chelator enhancing component(s), the masking agents are suppressed.

30 Claims, 7 Drawing Sheets

U.S. PATENT DOCUMENTS

| | | | |
|---|---|---|---|
| 4,882,270 A | 11/1989 | Moroz | 435/7 |
| 4,935,342 A | 6/1990 | Seligson et al. | 435/6 |
| 4,983,523 A | 1/1991 | Li et al. | 435/173 |
| 4,991,104 A | 2/1991 | Miller | 364/476 |
| 5,010,183 A | 4/1991 | Macfarlane | 536/27 |
| 5,030,720 A * | 7/1991 | Bertland et al. | 530/413 |
| 5,128,247 A | 7/1992 | Koller | 435/91 |
| 5,149,653 A | 9/1992 | Roser | 435/260 |
| 5,155,018 A | 10/1992 | Gillespie et al. | 435/91 |
| 5,192,553 A | 3/1993 | Boyse et al. | 424/529 |
| 5,217,866 A | 6/1993 | Summerton et al. | 435/6 |
| 5,234,809 A | 8/1993 | Boom et al. | 435/91 |
| 5,300,424 A | 4/1994 | Hoss et al. | 435/7.1 |
| 5,300,635 A | 4/1994 | Macfarlane | 536/25.4 |
| 5,312,744 A | 5/1994 | Shibata | 435/174 |
| 5,341,692 A | 8/1994 | Sher et al. | 73/864.63 |
| 5,346,999 A | 9/1994 | Cathcart et al. | 536/25.41 |
| 5,395,498 A | 3/1995 | Gombinsky et al. | 204/182.8 |
| 5,431,952 A | 7/1995 | Ocello | 427/4 |
| 5,457,025 A | 10/1995 | Collins et al. | 435/6 |
| 5,459,073 A | 10/1995 | Ryan | 436/16 |
| 5,459,253 A | 10/1995 | Wolin et al. | 536/25.42 |
| 5,464,744 A | 11/1995 | Farrell et al. | 435/6 |
| 5,501,963 A | 3/1996 | Burckhardt | 435/91.2 |
| 5,514,551 A * | 5/1996 | Yang et al. | 435/6 |
| 5,538,870 A | 7/1996 | Noeth et al. | 435/91.2 |
| 5,552,325 A | 9/1996 | Nochumson et al. | 436/177 |
| 5,554,503 A | 9/1996 | Down et al. | 435/6 |
| 5,595,896 A | 1/1997 | Coruzzi et al. | 435/172.3 |
| 5,609,864 A | 3/1997 | Shanbrom | 424/78.08 |
| 5,610,287 A | 3/1997 | Nikiforov et al. | 536/24.3 |
| 5,614,391 A | 3/1997 | Franciskovich et al. | 435/91.3 |
| 5,620,852 A | 4/1997 | Lin et al. | 435/6 |
| 5,629,147 A | 5/1997 | Asgari et al. | 435/5 |
| 5,637,687 A | 6/1997 | Wiggins | 536/25.4 |
| 5,643,767 A | 7/1997 | Fischetti et al. | 435/91.3 |
| 5,654,179 A | 8/1997 | Lin | 435/91.2 |
| 5,667,963 A | 9/1997 | Smith et al. | 435/2 |
| 5,702,896 A | 12/1997 | Collins et al. | 435/6 |
| 5,716,785 A | 2/1998 | Van Gelder et al. | 435/6 |
| 5,728,822 A | 3/1998 | Macfarlane | 536/25.41 |
| 5,744,302 A | 4/1998 | Sessler et al. | 435/6 |
| 5,744,520 A | 4/1998 | Kmiecik-Lawrynowicz et al. | 523/334 |
| 5,747,663 A | 5/1998 | Colpan et al. | 536/25.4 |
| 5,753,433 A | 5/1998 | Kessler et al. | 435/6 |
| 5,759,777 A | 6/1998 | Kearney et al. | 435/6 |
| 5,763,185 A * | 6/1998 | Collis et al. | 435/6 |
| 5,766,843 A | 6/1998 | Asgari et al. | 435/5 |
| 5,777,098 A | 7/1998 | Gray et al. | 536/25.41 |
| 5,777,099 A | 7/1998 | Mehra | 536/25.42 |
| 5,783,686 A | 7/1998 | Gonzalez | 536/25.4 |
| 5,784,162 A | 7/1998 | Cabib et al. | 356/346 |
| 5,786,208 A | 7/1998 | Clark et al. | 430/270 |
| 5,792,651 A | 8/1998 | Colpan et al. | 435/270 |
| 5,804,684 A | 9/1998 | Su | 536/25.4 |
| 5,808,041 A | 9/1998 | Padhye et al. | 536/25.4 |
| 5,811,099 A | 9/1998 | Ryan | 424/184.1 |
| 5,817,798 A | 10/1998 | Gundling | 536/25.42 |
| 5,830,664 A | 11/1998 | Rosemeyer et al. | 435/6 |
| 5,834,303 A | 11/1998 | Fujishiro | 435/287.7 |
| 5,837,466 A | 11/1998 | Lane et al. | 435/6 |
| 5,846,783 A | 12/1998 | Wu et al. | 425/91.2 |
| 5,849,517 A | 12/1998 | Ryan | 435/40.51 |
| 5,857,462 A | 1/1999 | Thomas et al. | 128/633 |
| 5,858,649 A | 1/1999 | Asgari et al. | 435/5 |
| 5,860,937 A | 1/1999 | Cohen | 600/576 |
| 5,861,253 A | 1/1999 | Asgari et al. | 435/6 |
| 5,871,928 A | 2/1999 | Fodor et al. | 435/6 |
| 5,879,875 A | 3/1999 | Wiggins et al. | 435/1.1 |
| 5,891,636 A | 4/1999 | Van Gelder et al. | 435/6 |
| 5,906,744 A | 5/1999 | Carroll et al. | 210/516 |
| 5,910,246 A | 6/1999 | Walter et al. | 210/232 |
| 5,916,775 A | 6/1999 | Hayashizaki | 435/91.1 |
| 5,932,422 A | 8/1999 | Shyjan et al. | 435/6 |
| 5,939,259 A * | 8/1999 | Harvey et al. | 435/6 |
| 5,945,515 A | 8/1999 | Chomczynski | 530/412 |
| 5,968,746 A | 10/1999 | Schneider | 435/6 |
| 5,972,222 A | 10/1999 | Gjerde et al. | 210/635 |
| 5,972,613 A | 10/1999 | Somack et al. | 435/6 |
| 5,973,137 A * | 10/1999 | Heath | 536/25.4 |
| 5,985,556 A | 11/1999 | Kambara et al. | 435/6 |
| 5,985,572 A | 11/1999 | Macfarlane | 435/6 |
| 5,990,301 A | 11/1999 | Colpan et al. | 536/25.4 |
| 5,990,302 A | 11/1999 | Kuroita et al. | 536/25.4 |
| 6,001,610 A | 12/1999 | Seibl et al. | 435/91.2 |
| 6,004,762 A | 12/1999 | Tse et al. | 435/7.23 |
| 6,020,186 A | 2/2000 | Henco et al. | 435/287.2 |
| 6,027,750 A | 2/2000 | Gautsch et al. | 424/489 |
| 6,027,890 A | 2/2000 | Ness et al. | 435/6 |
| 6,030,527 A | 2/2000 | Gjerde et al. | 210/198.2 |
| 6,030,608 A | 2/2000 | Hoyes et al. | 424/76.1 |
| 6,032,474 A | 3/2000 | Dale et al. | 62/239 |
| 6,037,465 A | 3/2000 | Hillebrand et al. | 536/25.42 |
| 6,043,032 A | 3/2000 | Yamagishi | 435/6 |
| 6,043,354 A | 3/2000 | Hillebrand et al. | 536/25.42 |
| 6,066,455 A | 5/2000 | Kruse-Mueller et al. | 435/6 |
| 6,071,395 A | 6/2000 | Lange | 204/602 |
| 6,071,745 A | 6/2000 | Lin et al. | 435/374 |
| 6,084,091 A | 7/2000 | Müller et al. | 536/25.4 |
| 6,090,936 A | 7/2000 | Walter et al. | 536/25.4 |
| 6,110,676 A | 8/2000 | Coull et al. | 435/6 |
| 6,111,096 A | 8/2000 | Laugharn, Jr. et al. | 536/25.4 |
| 6,114,108 A | 9/2000 | Budowsky | 435/2 |
| 6,117,398 A | 9/2000 | Bienhaus et al. | 422/101 |
| 6,120,985 A | 9/2000 | Laugharn, Jr. et al. | 435/1.3 |
| 6,121,055 A | 9/2000 | Hargreaves | 436/526 |
| 6,133,036 A | 10/2000 | Putcha et al. | 436/18 |
| 6,136,555 A | 10/2000 | Jones | 435/41 |
| 6,156,206 A | 12/2000 | Gjerde et al. | 210/635 |
| 6,165,773 A | 12/2000 | New et al. | 435/235.1 |
| 6,168,922 B1 * | 1/2001 | Harvey et al. | 435/6 |
| 6,177,278 B1 | 1/2001 | Haj-Ahmad | 436/94 |
| 6,197,506 B1 | 3/2001 | Fodor et al. | 435/6 |
| 6,203,993 B1 | 3/2001 | Shuber et al. | 435/6 |
| 6,210,881 B1 | 4/2001 | Little et al. | 435/6 |
| 6,218,531 B1 | 4/2001 | Ekenberg | 536/25.41 |
| 6,225,052 B1 | 5/2001 | Batz et al. | 435/6 |
| 6,231,815 B1 | 5/2001 | Bainczyk et al. | 422/102 |
| 6,232,464 B1 | 5/2001 | Lange | 536/25.4 |
| 6,235,501 B1 | 5/2001 | Gautsch et al. | 435/91.1 |
| 6,248,522 B1 | 6/2001 | Haberhausen et al. | 435/6 |
| 6,248,585 B1 | 6/2001 | Berd | 435/325 |
| 6,248,588 B1 | 6/2001 | Crespo et al. | 435/404 |
| 6,251,638 B1 | 6/2001 | Umansky et al. | 435/91.2 |
| 6,251,660 B1 | 6/2001 | Muir et al. | 435/287.2 |
| 6,258,320 B1 | 7/2001 | Persing et al. | 422/40 |
| 6,258,930 B1 | 7/2001 | Gauch et al. | 530/300 |
| 6,268,136 B1 | 7/2001 | Shuber et al. | 435/6 |
| 6,274,308 B1 | 8/2001 | Lee et al. | 435/5 |
| 6,274,386 B1 | 8/2001 | Harttig | 436/526 |
| 6,280,724 B1 | 8/2001 | Moore | 424/93.7 |
| 6,281,002 B1 | 8/2001 | Möller-Bremer | 435/262.5 |
| 6,281,349 B1 | 8/2001 | Pulleyblank | 536/25.4 |
| 6,287,820 B1 | 9/2001 | Umansky et al. | 435/61.1 |
| 6,291,178 B1 | 9/2001 | Schneider | 435/6 |
| 6,291,248 B1 | 9/2001 | Haj-Ahmad | 436/94 |
| 6,303,315 B1 | 10/2001 | Skouv | 435/6 |
| 6,306,345 B1 | 10/2001 | Bronshtein et al. | 422/41 |
| 6,322,981 B1 | 11/2001 | Rodgers et al. | 435/6 |
| 6,331,527 B1 | 12/2001 | Parmacek et al. | 514/44 |
| 6,342,387 B1 | 1/2002 | Hayashizaki et al. | 435/270 |
| 6,348,336 B1 | 2/2002 | Matveld et al. | 435/91.2 |
| 6,352,838 B1 | 3/2002 | Krulevitch et al. | 435/34 |

| | | | |
|---|---|---|---|
| 6,355,792 B1 | 3/2002 | Michelsen et al. ......... 536/25.4 |
| 6,391,541 B1 | 5/2002 | Petersen et al. ............... 435/5 |
| 6,409,528 B1 | 6/2002 | Bodnar ........................ 439/177 |
| 6,410,321 B1 | 6/2002 | Lin et al. .................... 435/374 |
| 6,458,546 B1 * | 10/2002 | Baker ............................. 435/6 |
| 6,465,209 B1 | 10/2002 | Blinkovsky et al. ........ 435/68.1 |
| 6,465,639 B1 | 10/2002 | van Gemen et al. ........ 536/25.4 |
| 6,468,782 B1 | 10/2002 | Tunnacliffe et al. ......... 435/260 |
| 6,471,866 B1 | 10/2002 | Gjerde et al. ................ 210/635 |
| 6,478,967 B1 | 11/2002 | Müller ....................... 210/650 |
| 6,492,162 B1 | 12/2002 | Sakurai et al. ........... 435/285.1 |
| 6,509,146 B1 | 1/2003 | Bronshtein ................. 435/1.3 |
| 6,514,943 B2 | 2/2003 | Kovesdi et al. ............... 514/23 |
| 6,528,641 B2 | 3/2003 | Lader ....................... 536/25.4 |
| 6,537,745 B2 | 3/2003 | Chien et al. .................... 435/5 |
| 6,541,204 B2 | 4/2003 | Nilsen et al. .................... 435/6 |
| 6,545,144 B2 | 4/2003 | Kolzau et al. .............. 536/25.4 |
| 6,548,256 B2 | 4/2003 | Lienau et al. .................... 435/6 |
| 6,551,777 B1 | 4/2003 | Shuber et al. .................... 435/6 |
| 6,562,573 B2 | 5/2003 | Halaka ............................ 435/6 |
| 6,602,718 B1 | 8/2003 | Augello et al. .............. 436/176 |
| 6,610,475 B1 | 8/2003 | Kacian et al. .................... 435/6 |
| 6,613,895 B1 | 9/2003 | Gautsch et al. ............ 536/25.4 |
| 6,617,170 B2 | 9/2003 | Augello et al. .............. 436/176 |
| 6,632,844 B1 | 10/2003 | Landt ........................ 514/693 |
| 6,635,420 B1 | 10/2003 | Hosel et al. .................... 435/6 |
| 6,649,378 B1 | 11/2003 | Kozwich et al. ............ 435/91.2 |
| 6,653,062 B1 | 11/2003 | DePablo et al. .............. 435/1.2 |
| 6,664,099 B1 | 12/2003 | Worrall ...................... 435/260 |
| 6,664,379 B1 | 12/2003 | Kudlicki et al. ........... 530/387.9 |
| 6,673,547 B2 | 1/2004 | Hirabayashi et al. ........... 435/6 |
| 6,673,631 B1 | 1/2004 | Tereba et al. ............... 436/526 |
| 6,686,460 B2 | 2/2004 | Lin et al. .................... 536/25.4 |
| 6,692,695 B1 | 2/2004 | Bronshtein et al. ............ 422/41 |
| 6,703,228 B1 | 3/2004 | Landers et al. .............. 435/91.2 |
| 6,706,498 B2 | 3/2004 | Gautsch et al. ............ 435/91.1 |
| 6,714,805 B2 | 3/2004 | Jeon et al. .................... 600/323 |
| 6,716,392 B1 | 4/2004 | Putcha et al. ................ 435/61 |
| 6,734,008 B2 | 5/2004 | Blanche et al. .......... 435/235.1 |
| 6,737,235 B1 | 5/2004 | Cros et al. ...................... 435/6 |
| 6,750,005 B2 | 6/2004 | Leif et al. ....................... 435/4 |
| 6,776,959 B1 | 8/2004 | Helftenbein ................. 422/50 |
| 6,780,584 B1 | 8/2004 | Edman et al. .................... 435/6 |
| 6,791,674 B2 | 9/2004 | Kawano ...................... 356/39 |
| 6,794,124 B2 | 9/2004 | Steen ........................... 435/1.1 |
| 6,794,140 B1 | 9/2004 | Goldsborough ............... 435/6 |
| 6,811,981 B2 | 11/2004 | Martin et al. .................... 435/6 |
| 6,812,341 B1 | 11/2004 | Conrad .................... 536/25.4 |
| 6,815,541 B1 | 11/2004 | Usui et al. ................ 536/25.41 |
| 6,821,789 B2 | 11/2004 | Augello et al. .............. 436/176 |
| 6,841,168 B1 | 1/2005 | Worrall ...................... 424/484 |
| 6,852,851 B1 | 2/2005 | Tooke et al. ................ 536/25.4 |
| 6,861,213 B2 | 3/2005 | Oelmüller et al. ............... 435/5 |
| 6,864,046 B1 | 3/2005 | Prien et al. ...................... 435/2 |
| 6,872,527 B2 | 3/2005 | Gerdes et al. .................... 435/6 |
| 6,905,825 B2 | 6/2005 | Kojima et al. ................... 435/6 |
| 6,914,137 B2 | 7/2005 | Baker ........................ 536/25.4 |
| 6,919,172 B2 | 7/2005 | DePablo et al. ............. 435/1.1 |
| 6,919,175 B1 | 7/2005 | Bienhaus et al. ................. 435/6 |
| 6,927,045 B2 | 8/2005 | Hadd et al. ................ 435/91.2 |
| 6,936,414 B2 | 8/2005 | Gundling ......................... 435/6 |
| 6,939,762 B2 | 9/2005 | Tsugane et al. ............. 438/253 |
| 6,946,252 B2 | 9/2005 | Kambara ........................ 435/6 |
| 6,958,392 B2 | 10/2005 | Fomovskaia et al. ..... 536/25.42 |
| 6,962,778 B1 | 11/2005 | Coull et al. ...................... 435/6 |
| 6,969,603 B2 | 11/2005 | Hayashizaki et al. ........ 435/270 |
| 6,972,329 B2 | 12/2005 | Burgoyne ................... 536/25.4 |
| 6,979,573 B2 | 12/2005 | Huang ........................ 436/518 |
| 6,986,848 B2 | 1/2006 | Ikeda et al. ................. 210/695 |
| 6,992,182 B1 | 1/2006 | Müller et al. ............ 536/25.41 |
| 6,999,181 B2 | 2/2006 | Dulman ....................... 356/512 |
| 7,005,266 B2 | 2/2006 | Sprenger-Haussels ........... 435/6 |
| 7,022,514 B2 | 4/2006 | Vodyanoy et al. ........... 435/260 |
| 7,025,876 B2 | 4/2006 | Shoji et al. ................. 210/198.2 |
| 7,029,627 B2 | 4/2006 | Alley ............................ 422/58 |
| 7,029,840 B2 | 4/2006 | McMillian ..................... 435/2 |
| 7,052,864 B2 | 5/2006 | Durkop et al. ................ 435/25 |
| 7,056,673 B2 | 6/2006 | Kamme et al. .................. 435/6 |
| 7,060,804 B2 | 6/2006 | Elaissari et al. .............. 530/412 |
| 7,067,287 B1 | 6/2006 | Sakurai et al. .............. 435/91.1 |
| 7,076,960 B2 | 7/2006 | Takemasa .......................... 62/6 |
| 7,087,387 B2 | 8/2006 | Gerdes et al. .................... 435/6 |
| 7,090,804 B2 | 8/2006 | Kayyem et al. ............. 422/68.1 |
| 7,091,030 B2 | 8/2006 | Setiawan et al. .......... 435/235.1 |
| 7,097,980 B2 | 8/2006 | Barany et al. .................... 435/6 |
| 7,105,318 B2 | 9/2006 | Kessler et al. .............. 435/91.2 |
| 7,113,814 B2 | 9/2006 | Ward et al. .................. 600/310 |
| 7,115,719 B2 | 10/2006 | Paulsen ...................... 530/427 |
| 7,143,103 B1 | 11/2006 | Zisman et al. .............. 707/102 |
| 7,270,953 B2 | 9/2007 | Holländer et al. ............... 435/6 |
| 2001/0000635 A1 | 5/2001 | Reo ............................ 264/255 |
| 2001/0018412 A1 | 8/2001 | Kambara ....................... 514/1 |
| 2001/0019824 A1 | 9/2001 | Kambara ........................ 435/6 |
| 2001/0020153 A1 | 9/2001 | Howell .................... 604/167.04 |
| 2002/0009727 A1 | 1/2002 | Schultz et al. .................. 435/6 |
| 2002/0102570 A1 | 8/2002 | Baker ............................. 435/6 |
| 2002/0102580 A1 | 8/2002 | Baker ............................. 435/6 |
| 2002/0102600 A1 | 8/2002 | Kambara ........................ 435/6 |
| 2002/0119478 A1 | 8/2002 | Umansky ........................ 435/6 |
| 2002/0132235 A1 | 9/2002 | Avihingsanon et al. ......... 435/6 |
| 2002/0132992 A1 | 9/2002 | Leif et al. ..................... 534/615 |
| 2002/0137027 A1 | 9/2002 | Durkop ........................... 435/5 |
| 2002/0137196 A1 | 9/2002 | Miles et al. ............... 435/287.2 |
| 2002/0146677 A1 | 10/2002 | Augello et al. .................. 435/2 |
| 2002/0150907 A1 | 10/2002 | Fomovskaia et al. ............ 435/6 |
| 2002/0151073 A1 | 10/2002 | Christensen ................ 435/484 |
| 2002/0160137 A1 | 10/2002 | Varma ....................... 428/35.7 |
| 2002/0164572 A1 | 11/2002 | Lin et al. ......................... 435/2 |
| 2002/0164631 A1 | 11/2002 | Shuber et al. ................... 435/6 |
| 2002/0197631 A1 | 12/2002 | Lawrence et al. ............... 435/6 |
| 2003/0009090 A1 | 1/2003 | Jeon et al. .................... 600/323 |
| 2003/0039661 A1 | 2/2003 | Aja et al. .................... 424/186.1 |
| 2003/0057154 A1 | 3/2003 | Gjerde et al. ................ 210/635 |
| 2003/0082649 A1 | 5/2003 | Weich et al. ............... 435/7.21 |
| 2003/0086380 A1 | 5/2003 | Kim et al. .................... 370/280 |
| 2003/0104371 A1 | 6/2003 | Strom et al. ..................... 435/6 |
| 2003/0114651 A1 | 6/2003 | Lader ........................ 536/23.1 |
| 2003/0138415 A1 | 7/2003 | Shepard ...................... 424/94.4 |
| 2003/0148500 A1 | 8/2003 | Christensen ............... 435/254.3 |
| 2003/0166512 A1 | 9/2003 | Xie ................................ 514/7 |
| 2003/0201239 A1 | 10/2003 | Hudak et al. ................ 215/247 |
| 2003/0204331 A1 | 10/2003 | Whitney et al. ............... 702/32 |
| 2003/0211452 A1 | 11/2003 | Vincek et al. ................ 435/1.1 |
| 2003/0211503 A1 | 11/2003 | Carpentieri ..................... 435/6 |
| 2003/0215358 A1 | 11/2003 | Schulman et al. ............. 422/56 |
| 2003/0228613 A1 | 12/2003 | Bornarth et al. ................. 435/6 |
| 2003/0232377 A1 | 12/2003 | Thomas .......................... 435/6 |
| 2004/0013575 A1 | 1/2004 | Stevens et al. ............... 422/102 |
| 2004/0025193 A1 | 2/2004 | Echelard et al. ................. 800/6 |
| 2004/0039269 A1 | 2/2004 | Ward et al. .................. 600/312 |
| 2004/0043374 A1 | 3/2004 | DePablo et al. ............. 435/1.1 |
| 2004/0043505 A1 | 3/2004 | Walenciak et al. .......... 436/174 |
| 2004/0048384 A1 | 3/2004 | Augello et al. ................ 436/18 |
| 2004/0053318 A1 | 3/2004 | McWilliams et al. ........... 435/6 |
| 2004/0076990 A1 | 4/2004 | Picard et al. .................... 435/6 |
| 2004/0097455 A1 | 5/2004 | Borunda et al. ............... 514/44 |
| 2004/0115658 A1 | 6/2004 | Weber et al. .................... 435/6 |
| 2004/0115689 A1 | 6/2004 | Augello et al. .................. 435/6 |
| 2004/0126280 A1 | 7/2004 | Leaman, Jr. ................. 422/102 |
| 2004/0126764 A1 | 7/2004 | Lasken et al. ................... 435/6 |
| 2004/0126796 A1 | 7/2004 | Carlson et al. ................... 435/6 |
| 2004/0137417 A1 | 7/2004 | Ryan ............................. 435/2 |
| 2004/0157211 A1 | 8/2004 | Skyggebjerg et al. ........... 435/5 |
| 2004/0214200 A1 | 10/2004 | Brown et al. .................... 435/6 |
| 2004/0234423 A1 | 11/2004 | Dehmer ...................... 422/102 |
| 2004/0235065 A1 | 11/2004 | Hansen et al. .............. 435/7.21 |

| | | | | | | |
|---|---|---|---|---|---|---|
| 2004/0265786 A1 | 12/2004 | Lin et al. ............... 435/2 | | 2006/0147957 A1 | 7/2006 | Qian et al. ............. 435/6 |
| 2004/0265840 A1 | 12/2004 | Kunitake et al. ......... 435/6 | | 2006/0166205 A1 | 7/2006 | Salonen et al. ........... 435/6 |
| 2005/0003390 A1 | 1/2005 | Axenovich et al. ........ 435/6 | | 2006/0166258 A1 | 7/2006 | Kamme et al. ........... 435/6 |
| 2005/0019769 A1 | 1/2005 | Lenz ................... 435/6 | | 2006/0167401 A1 | 7/2006 | Cohen ............... 604/6.15 |
| 2005/0019902 A1 | 1/2005 | Mathies et al. ....... 435/287.2 | | 2006/0172332 A1 | 8/2006 | Vodyanoy et al. .......... 435/6 |
| 2005/0026153 A1 | 2/2005 | Iannotti et al. ........ 435/6 | | 2006/0204950 A1 | 9/2006 | Ilercil et al. ............ 435/1.1 |
| 2005/0026186 A1 | 2/2005 | Yamaya et al. .......... 435/6 | | 2006/0210988 A1 | 9/2006 | Inose et al. ............. 435/6 |
| 2005/0054103 A1 | 3/2005 | Peled et al. ........... 435/455 | | 2006/0228693 A1 | 10/2006 | Soll ................. 435/1.1 |
| 2005/0074796 A1 | 4/2005 | Yue et al. ............. 435/6 | | 2006/0231519 A1 | 10/2006 | Py et al. ............. 215/342 |
| 2005/0079484 A1 | 4/2005 | Heineman et al. ........ 435/5 | | 2006/0234243 A1 | 10/2006 | Bestmann ............. 435/6 |
| 2005/0084983 A1 | 4/2005 | Gabizon et al. ......... 436/518 | | 2007/0015165 A1 | 1/2007 | Chen et al. ............ 435/6 |
| 2005/0106612 A1 | 5/2005 | Amirkhanian et al. ...... 435/6 | | 2007/0087369 A1 | 4/2007 | Chen et al. ............ 435/6 |
| 2005/0112572 A1 | 5/2005 | Pincemail et al. ........ 435/6 | | 2008/0064108 A1* | 3/2008 | Baker ............... 436/18 |
| 2005/0124965 A1 | 6/2005 | Haywood ............... 604/500 | | | | |
| 2005/0129572 A1 | 6/2005 | Schulman et al. ......... 422/56 | | | | |
| 2005/0132775 A1 | 6/2005 | Laugharn, Jr. et al. ...... 73/12.01 | | | | |
| 2005/0156378 A1 | 7/2005 | Steinhardt ............. 273/108.1 | | | | |
| 2005/0164215 A1 | 7/2005 | Hofstadler et al. ....... 435/6 | | | | |
| 2005/0170375 A1 | 8/2005 | Scherf et al. .......... 435/6 | | | | |
| 2005/0176027 A1 | 8/2005 | Suzow et al. .......... 435/6 | | | | |
| 2005/0181386 A1 | 8/2005 | Diamond et al. ......... 435/6 | | | | |
| 2005/0191508 A1 | 9/2005 | McEntee .............. 428/577 | | | | |
| 2005/0208534 A1 | 9/2005 | Dallwig et al. .......... 435/6 | | | | |
| 2005/0214810 A1 | 9/2005 | Dallwig et al. .......... 435/6 | | | | |
| 2005/0221310 A1 | 10/2005 | Scherf et al. .......... 435/6 | | | | |
| 2005/0244837 A1 | 11/2005 | McMillan ............. 435/6 | | | | |
| 2005/0266391 A1 | 12/2005 | Bennett et al. .......... 435/1.1 | | | | |
| 2005/0282202 A1 | 12/2005 | Brolaski et al. ......... 435/6 | | | | |
| 2005/0287513 A1 | 12/2005 | Davis et al. ........... 435/2 | | | | |
| 2005/0288227 A1 | 12/2005 | Marks et al. ........... 514/12 | | | | |
| 2006/0014177 A1 | 1/2006 | Hogan et al. ........... 435/6 | | | | |
| 2006/0014214 A1 | 1/2006 | Baker ................ 435/7.1 | | | | |
| 2006/0021673 A1 | 2/2006 | Rodewald ............. 141/127 | | | | |
| 2006/0024838 A1 | 2/2006 | Leaman, Jr. ........... 436/176 | | | | |
| 2006/0040293 A1 | 2/2006 | Salonen et al. .......... 435/6 | | | | |
| 2006/0073509 A1 | 4/2006 | Kilpatrick et al. ....... 435/6 | | | | |
| 2006/0081554 A1 | 4/2006 | Snyder ............... 215/364 | | | | |
| 2006/0094015 A1 | 5/2006 | Smith et al. ........... 435/6 | | | | |
| 2006/0099567 A1 | 5/2006 | Muller-Cohn et al. ...... 435/1.1 | | | | |
| 2006/0099605 A1 | 5/2006 | Hall, Jr. et al. .......... 435/6 | | | | |
| 2006/0099610 A1 | 5/2006 | Salonen et al. .......... 435/6 | | | | |
| 2006/0105347 A1 | 5/2006 | Meade et al. ........... 435/6 | | | | |
| 2006/0105353 A1 | 5/2006 | Jalal et al. ............ 435/6 | | | | |
| 2006/0105370 A1 | 5/2006 | Hashmi et al. .......... 435/6 | | | | |
| 2006/0105468 A1 | 5/2006 | Winkler et al. .......... 436/174 | | | | |
| 2006/0110751 A1 | 5/2006 | Salonen et al. .......... 435/6 | | | | |
| 2006/0123500 A1 | 6/2006 | Echelard et al. ......... 800/14 | | | | |
| 2006/0127507 A1 | 6/2006 | Yoshida et al. .......... 424/738 | | | | |
| 2006/0127902 A1 | 6/2006 | Madden et al. ......... 435/6 | | | | |
| 2006/0141488 A1 | 6/2006 | Huang et al. ........... 435/6 | | | | |
| 2006/0144869 A1 | 7/2006 | Chang et al. ........... 222/386 | | | | |
| 2006/0147918 A1 | 7/2006 | Goldsborough .......... 435/6 | | | | |
| 2006/0147944 A1 | 7/2006 | Chomczynski .......... 435/6 | | | | |

FOREIGN PATENT DOCUMENTS

| | | | |
|---|---|---|---|
| EP | 0818542 | 7/1997 | |
| EP | 1207208 | 5/2002 | |
| EP | 1584923 | 10/2005 | |
| WO | WO 93/03167 | * 2/1993 | ............ 436/91.1 |
| WO | 9418156 | 8/1994 | |
| WO | WO 95/35390 | * 12/1995 | ............... 435/6 |
| WO | 9929904 | 6/1999 | |
| WO | 00/09746 | 2/2000 | |
| WO | 02/00600 | 6/2001 | |
| WO | 02/00059 | 1/2002 | |
| WO | 03067978 | 8/2003 | |

OTHER PUBLICATIONS

Akane et al., Journal of Forensic Sciences; vol. 39, pp. 362-372; 1994.*

Ahern, Holly; The Scientist; vol. 9, 1995, from the internet; pp. 1-5.*

Chung, C. H. et al. Mol. Cells 6(1):108-111 (1996).*

Bection, Dickinson and Company; 510(k) Summary; BD ProbTec ET *Chlamydia trachomatis* and *Neisseria gonorrhoeae* Amplified DNA Assay; BD Diagnostic Systems, pp. 5.

BD- DIagnostic Systems: BD ProbeTec Urine Preservative Transport Kit; www.bd.com; pp. 2.

Qiagen—PAXgene Blood DNA Tubes—For blood collection prior to genomic DNA purification using the PAXgene Blood Kit; www1.qiagen.com; pp. 3.

PreAnalytiX; PAXgene; Blood RNA Tube; www.PreAnalytiX.com; pp. 5.

PreAnalytiX; PAXgene Blood DNA Tube, For the Collection of Whole Blood for enomic DNA Isolation; Catalog No. 769989; pp. 10.

PreAnalytiX; PAXgene, Blood RNA Kit Handbook; Catalog No. 762164; pp. 35.

Difco Product Catalog; GC Medium Base, GC Base, GC II Agar Base, Supplement B, Supplament VX, Iso VitaleX Enrichment, Hemoglobin, Antimicrobic CNV, VCN Inhibitor, VCNT Inhibitor, VCA Inhibitor, VCAT Inhibitor; pp. 5.

* cited by examiner

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Artificial Sequence (primer)

<400> SEQUENCE: 1
agttatctac acgacgc                                                17

<210> SEQ ID NO 2

-continued

```
<211> LENGTH: 17
<212> TYPE: DNA
<213> ORGANISM: Artificial Sequence
<220> FEATURE:
<223> OTHER INFORMATION: Artificial Sequence (primer)

<400> SEQUENCE: 2
ggcgtactat tcactct                                                  17

<210> SEQ ID NO 3
<211> LENGTH: 25
<212> TYPE: DNA
<213> ORGANISM: Artificial Sequence
<220> FEATURE:
<223> OTHER INFORMATION: Artificial Sequence (primer)

<400> SEQUENCE: 3
gcgtcagacc cctatctata aactc                                         25
```

REMOVAL OF MOLECULAR ASSAY INTERFERENCES

RELATED APPLICATIONS

This application is a continuation-in-part of application Ser. No. 09/805,785, filed Mar. 13, 2001, now abandoned, which is a continuation of application No. 09/185,402, filed Nov. 3, 1998, now abandoned, which is a continuation-in-part of application Ser. No. 08/988,029, filed Dec. 10, 1997, now abandoned. The entire contents of all the aforementioned applications are incorporated herein by reference.

BACKGROUND OF THE INVENTION

The present disclosure relates generally to the field of DNA analysis. More particularly, the present disclosure relates to methods and systems for removing interferences from test samples, e.g., DNA-containing samples obtained from living subjects, when they are submitted for or subjected to molecular assays.

The copying and cloning of virtually any nucleic acid sequence has been greatly facilitated by the polymerase chain reaction (PCR), which has become a fundamental methodology in molecular biology. In its simplest form, the PCR is an in vitro method for the enzymatic synthesis of specific DNA sequences. In brief, the PCR involves hybridizing primers to the denatured strands of a target nucleic acid or template in the presence of a polymerase enzyme and nucleotides under appropriate reaction conditions. The polymerase enzyme (usually a thermostable DNA polymerase) then recognizes the primer hybridized to the template and processes a primer extension product complementary to the template. The resultant template and primer extension product can then be subjected to further rounds of subsequent denaturation, primer hybridization, and extension as many times as desired in order to increase (or amplify) the amount of nucleic acid which has the same sequence as the target nucleic acid. Commercial vendors market PCR reagents and publish PCR protocols. The PCR is capable of producing a selective enrichment of a specific DNA sequence by a factor of $10^9$. The method is described in, e.g., U.S. Pat. Nos. 4,683,202; 4,683,195; 4,800,159; and 4,965,188, and in Saiki et al., 1985, *Science* 230: 1350.

The optimal efficiency of the amplification reaction, however, may be compromised by a number of unwanted side reactions. For example, many PCR procedures yield non-specific by-products caused by mispriming of the primers and template. Primers hybridizing to each other may also result in lost efficiency. This problem may be particularly acute when the target nucleic acid is present in very low concentrations and may obscure any amplified target nucleic acid (i.e., may produce high background).

Also, masking agents which interfere or inhibit such molecular assays as the PCR are a problem in the art. Such inhibitors, which include leukocyte esterases, heme proteins, e.g., myoglobin and hemoglobin analogs, oxidation and breakdown products such as ferritins, methemoglobin, sulf-hemoglobin and bilirubin, affect the accuracy of the assay, masking the true or detectable amount of, e.g., DNA in the sample. It is also conceivable that, e.g., a human sample containing genetic material for analysis could be spiked or doped with such agents to render a molecular assay done on the sample less trustworthy, or inconclusive.

Modem testing and treatment procedures have successfully reduced the prevalence and severity of many infectious diseases. For example, sexually-transmitted disease (STD) clinics regularly screen and treat patients for such diseases as gonorrhea and syphilis. Infectious agents such as gonococci may be identified by analyzing a DNA sample. Genetic transformation tests (GTT), such as the Gonostat® procedure (Sierra Diagnostics, Inc., Sonora, Calif.), can be used to detect gonococcal DNA in specimens taken from the urethra of men, and the cervix and anus of women. See, e.g., Jaffe et al., *Diagnosis of gonorrhea using a genetic transformation test on mailed clinical specimens*, J. Inf. Dis. 1982; 146:275-279, and Whittington et al., *Evaluation of the genetic transformation test,*. Abstr. Ann. Meeting. Am. Soc. Microbiol. 1983; p. 315. The Gonostat® assay is discussed in Zubrzycki et al., *Laboratory diagnosis of gonorrhea by a simple transformation test with a temperature-sensitive mutant of Neisseria gonorrhoeae*, Sex. Transm. Dis. 1980; 7:183-187. The Gonostat(3) GTT, for example, may be used to detect, e.g., gonococcal DNA in urine specimens. The Gonostat assay uses a test strain, *N. Gonorrhoeae*, ATCC 31953, which is a mutant strain that is unable to grow into visible colonies on chocolate agar at 37° C. in 5% $CO_2$. Gonococcal DNA extracted from clinical material can restore colony growth ability to this test strain.

Such tests such can be used to detect DNA in such bodily fluids and excretions as urine, blood, blood serum, amniotic fluids, spinal fluid, conjunctival fluid, salivary fluid, vaginal fluid, stool, seminal fluid, and sweat. Another test that can be used to identify DNA in a bodily fluid is the PCR, since it uses discrete nucleic acid sequences and therefore can be effective even in the absence of intact DNA.

SUMMARY OF THE INVENTION

The present invention relates to methods, systems and reagents for enabling and improving molecular assay of nucleic acids in bodily samples, e.g., fluids and excretions such as urine and blood to be carried out with greater sensitivity. It is believed, without limitation to a particular theory or view, that the methods and reagents remove or inactivate certain masking agents known to be interferents of molecular assays such as methemoglobin, such that they no longer interfere with the accuracy or sensitivity of the molecular assay. These methods and reagents have been found to also surprisingly increase the signal obtained with nucleic acid testing methods such as the polymerase chain reaction, $LC_x$, (Abbott Laboratories) and genetic transformation testing. An unexpected additional advantage of the invention is that hybridization in molecular assays such as nucleic acid testing methods is improved, compared to when such assays are carried out without employing the present invention.

In an embodiment, the invention relates to methods of suppressing the action of masking agents of molecular assays, with the result being that the assay may be carried out at a much higher confidence level. The masking agents that are present in a nucleic acid-containing test sample are suppressed by contacting the test sample with an amount of one or more divalent metal chelators like ethylenediaminetetraacetic acid or 1,2-bis(2-aminophenoxy)ethane-N,N,N',N'-tetraacetic acid, or salts thereof; and an amount of one or more chelator enhancing components like lithium chloride, guanidine, or sodium salicylate. The amounts of the divalent metal chelator(s) and the chelator enhancing component(s) are selected such that the masking agents are suppressed, and upon contact with the divalent metal chelator(s)/chelator enhancing component(s), the masking agents are suppressed. The amount of the divalent metal chelator is generally in the range of from about 0.001M to 0.1M, and the amount of the chelator enhancing component is generally in the range of from about 0.1M to 2M. The amount of chelator enhancing component is more desirably at least 1M, and the divalent metal chelator is desirably present in an amount of at least about 0.01M.

In another aspect, the invention relates to methods of improving the signal response of a molecular assay. The masking agents in a nucleic acid-containing test sample are suppressed by contacting the test sample with an amount of one or more divalent metal chelator(s); and an amount of one or more chelator enhancing components. The amounts of the divalent metal chelator(s) and chelator enhancing component(s) are selected such that the masking agents are suppressed. Molecular analytes of interest from the preserved test sample are then extracted; and a molecular assay is conducted on the extracted molecular analytes of interest, whereupon the signal response of the molecular assay is improved. Signal response is believed to be enhanced in part due to enhanced hybridization as a result of the use of the reagents of the present invention.

A further aspect of the invention relates to methods of improving hybridization of nucleic acids, including contacting a test nucleic acid with a reagent comprising an amount of at least one divalent metal chelator, e.g., in the range of from about 0.001M to 0.1M; and an amount of at least one chelator enhancing component, e.g., lithium chloride, guanidine, sodium salicylate, sodium perchlorate, or sodium thiocyanate, e.g., in the range of from about 0.1M to 2M, such that a test solution is formed; and contacting the test solution with a target nucleic acid under conditions favorable for hybridization, such that hybridization occurs.

The methods and reagents of the invention may further include an amount of at least one enzyme-inactivating component such as manganese chloride, sarkosyl, or sodium dodecyl sulfate, generally in the range of about 0-5% molar concentration.

Accordingly, in one aspect, the invention provides a method for amplifying target nucleic acids, including combining a target nucleic acid under conditions which allow for an amplification reaction to occur. The invention may also be useful in commercial applications including specialty chemicals and instrumentation for utilizing this technology, e.g., probe based diagnostics, microarray/DNA Chip methods, PCR (e.g., hot-start PCR) hybridization and amplification, SNP analysis, and DNA sequencing. Other applications include drug discovery and the study of drug response genes (pharmacogenomics), drug delivery and therapeutics.

An advantage of the invention is that no manipulation of the reaction mixture need be done following initial preparation. Thus, the invention may be used in existing automated PCR amplification systems and with in situ amplification methods where the addition of reagents after the initial denaturation step is inconvenient or impractical.

DETAILED DESCRIPTION OF THE INVENTION

Figure 1:
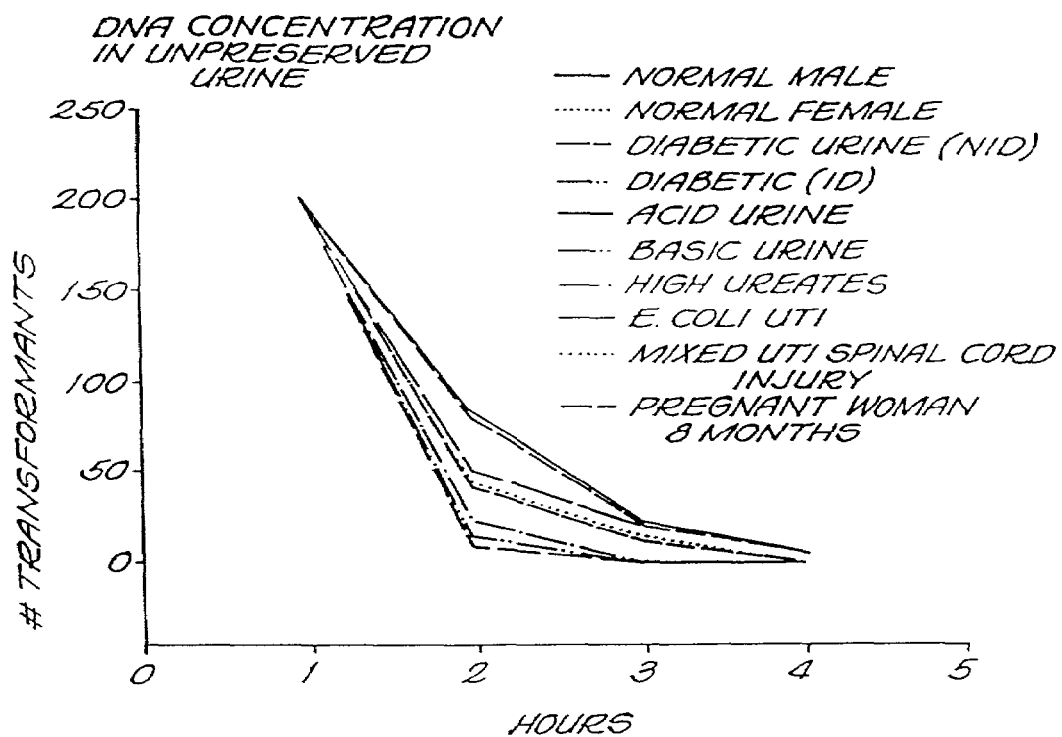
FIG. 1 is a graph of DNA concentration in urine according to the prior art.
Figure 2:
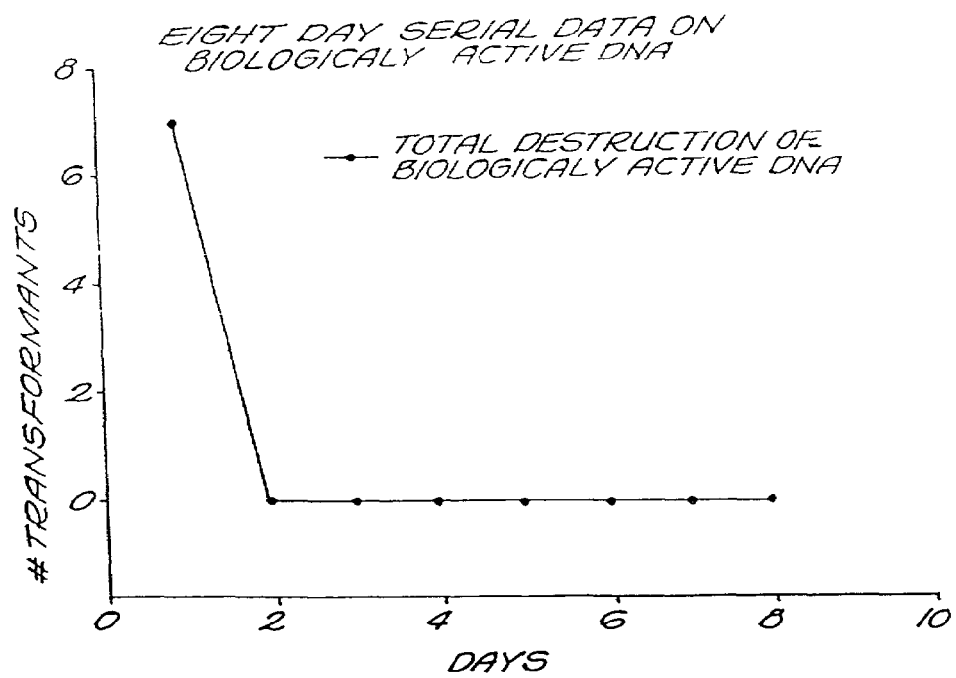
FIG. 2 is a graph of eight day serial data on urine according to the prior art.
Figure 3:
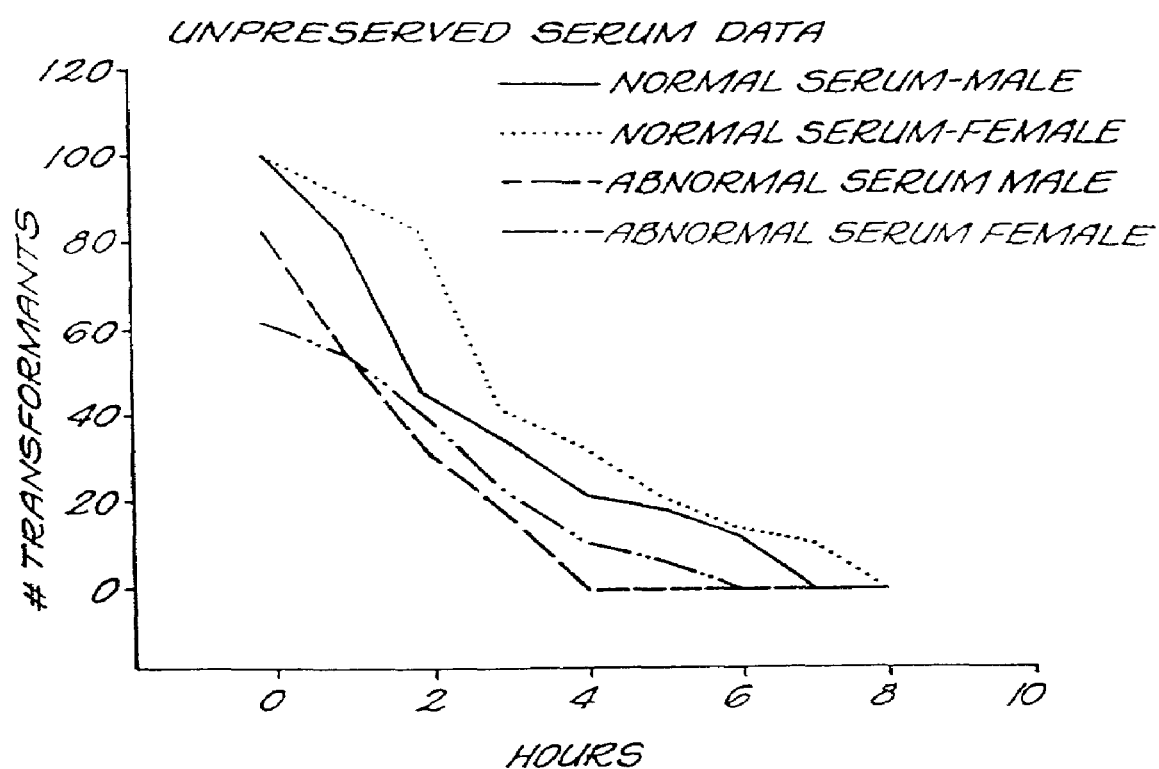
FIG. 3 is a graph of DNA concentration in serum according to the prior art.

"Molecular assay" includes nucleic acid amplification techniques such as the PCR; RT-PCR (e.g., U.S. Pat. No. 4,683,202); LCR (ligase chain reaction) described in, e.g., EP-A-0320308; the "NASBA" or "3SR" technique described in, e.g., *Proc. Natl. Acad. Sci.* Vol. 87 pp. 1874-1878 March 1990 and *Nature* Vol. 350, No. 634. PP 91-92 Mar. 7, 1991; the "SDA" method described in, e.g., *Nucleic Acid Research*, Vol. 20 PP 1691-1696; $LC_x$; and genetic transformation testing (GTT).

"Masking agents" or "interferents of molecular assay(s)" includes compounds which interfere or otherwise affect the accuracy of the assay, masking the true or detectable amount of the nucleic acid in the sample. Examples are leukocyte esterases, heme proteins such as myoglobin and hemoglobin analogs, derivatives, oxidation and breakdown products such as ferritins, methemoglobin, sulfhemoglobin and bilirubin. "Metal cations" include cations associated with metal dependent enzymes. Examples of metal cations include cations of iron, aluminum, copper, cobalt, nickel, zinc, cadmium, magnesium, and calcium. Metal cations of particular interest include magnesium (e.g., $Mg^{+2}$) and calcium (e.g., $Ca^{+2}$).

"Bodily fluid" includes e.g., urine, blood, blood serum, amniotic fluid; cerebrospinal and spinal fluid; fluid; synovial fluid; conjunctival fluid; salivary fluid; vaginal fluid; stool; seminal fluid; lymph; bile; tears, and sweat.

"Sample" includes substances containing or presumed to contain nucleic acid and may include a sample of tissue or fluid isolated from an individual or individuals, including bodily fluids, skin, blood cells, organs, tumors, and also to samples of in vitro cell culture constituents (including but not limited to conditioned medium resulting from the growth of cells in cell culture medium, recombinant cells and cell components).

"Divalent metal chelator" includes compounds which chelate or remove divalent metal cations such that metal dependent enzymes such as deoxyribonucleases are inactivated. Deoxyribonuclease, e.g., have been found to inactivate gonococcal DNA in urine over time. Suitable divalent metal chelators include ethylenediaminetetraacetic acid (EDTA), imidazole, ethylenebis(oxyethylenenitrilo]tetraacetic acid (EGTA); iminodiacetate (IDA); or 1,2- bis(2-aminophenoxy) ethane-N,N,N',N'-tetraacetic acid (BAPTA); bis(5-amidino-2- benzimidazolyl)methane (BABIM) or salts thereof. Preferred divalent metal chelators include EDTA and BAPTA. The amount of the divalent metal chelator that is generally present in a reagent solution is in the range of from about 0.001M to 0.1M. More desirably, the amount of the divalent metal chelator in the reagent solution is at least 0.01M.

"Chelator enhancing component" includes compounds which, inter alia, assist the divalent metal chelator in protecting the nucleic acids in the fluid. These chelator enhancing components are believed to inactivate metal independent enzymes found in samples, such as DNA ligases, e.g., D4 DNA ligase; DNA polymerases such as T7 DNA polymerase; exonucleases such as exonuclease 2, -exonuclease; kinases such as T4 polynucleotide kinase; phosphatases such as BAP and CIP phosphatase; nucleases such as BL31 nuclease and XO nuclease; and RNA-modifying enzymes such as *E coli* RNA polymerase, SP6, T7, T3 RNA polymerase, and T4 RNA ligase. Lithium chloride, guanidine, sodium salicylate, sodium perchlorate, and sodium thiocyanate have been found to be particularly effective. The amount of the chelator enhancing component is generally in the range of from about 0.1M to 2M, and more desirably the amount of chelator enhancing component in the reagent solution is at least 1M.

"Nucleic acid", "polynucleotide" and "oligonucleotide" include DNA molecules (e.g., cDNA or genomic DNA), RNA molecules (e.g., mRNA), analogs of the DNA or RNA generated using nucleotide analogs or using nucleic acid chemistry, and PNA (protein nucleic acids); modified nucleotides such as methylated or biotinylated nucleotides, primers, probes, oligomer fragments, oligomer controls and unlabeled blocking oligomers polydeoxyribonucleotides (containing 2-deoxy-D-ribose), polyribonucleotides (containing D-ribose), and any other type of polynucleotide which is an N-glycoside of a purine or pyrimidine base, or modified purine or pyrimidine base. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. Oligonucleotides typically include a sequence of approximately at least 6 nucleotides, preferably at least about 10-12 nucleotides, and more preferably at least about 15-20 nucleotides corresponding to a region of the designated nucleotide sequence.

Oligonucleotides are not necessarily physically derived from any existing or natural sequence but may be generated in any manner, including chemical synthesis, DNA replication, reverse transcription or a combination thereof. Oligonucleotides or nucleic acids can include those which, by virtue of its origin or manipulation: (1) are not associated with all or a portion of the polynucleotide with which it is associated in nature; and/or (2) are linked to a polynucleotide other than that to which it is linked in nature; and (3) are not found in nature.

"Corresponding" means identical to or complementary to the designated sequence.

"Primer" or "nucleic acid primer" may refer to more than one primer and includes oligonucleotides, whether occurring naturally, as in a purified restriction digest, or produced synthetically, which are capable of acting as a point of initiation of synthesis along a complementary strand when placed under conditions in which synthesis of a primer extension product which is complementary to a nucleic acid strand is catalyzed. Primers are typically between about 10 to 100 bases and are designed to hybridize with a corresponding template nucleic acid. Primer molecules may be complementary to either the sense or the anti-sense strand of a template nucleic acid and are typically used as complementary pairs that flank a nucleic acid region of interest. Synthesis conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The "complement" of a nucleic acid sequence includes oligonucleotides which, when aligned with the nucleic acid sequence such that the 5' end of one sequence is paired with the 3' end of the other, is in "antiparallel association." Certain bases not commonly found in natural nucleic acids may be included, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

"Target sequence" or "target nucleic acid sequence" refers to a region of the oligonucleotide which is to be either amplified, detected or both. The target sequence resides between the two primer sequences used for amplification.

"Probe" refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

"Polymerase" includes any one of, or a mixture of, the nucleotide polymerizing enzymes *E. coli* DNA polymerase I, TAQ polymerase, Klenow fragment of *E. coli* DNA polymerase I, T4 DNA polymerase, reverse transcriptase where the template is RNA and the extension product is DNA, or a thermostable DNA polymerase.

"Thermostable nucleic acid polymerase" refers to an enzyme which is relatively stable to heat when compared, for example, to nucleotide polymerases from *E. coli* and which catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. A preferred thermostable enzyme isolated from *Thermus aquaticus* (Taq) is described in U.S. Pat. No. 4,889,818 and a method for using it in conventional PCR is described in, e.g., Saiki et al., 1988, *Science* 239:487. Taq DNA polymerase has a DNA synthesis-dependent, strand replacement 5'-3' exonuclease activity (see Gelfand, "Taq DNA Polymerase" in *PCR Technology: Principles and Applications for DNA Amplification*, Erlich, Ed., Stockton Press, N.Y. (1989), Chapter 2). Additional representative temperature stable polymerases include polymerases extracted from the thermostable bacteria *Thermus flavus, Thermus ruber, Thermus thermophilus, Bacillus stearothermophilus, Thermus lacteus, Thermus rubens, Thermotoga maritima, Ther-*

*mococcus litoralis, Methanothermnus fervidus, Thermus filiformis, Thermus flavus, Pyrococcus furiosus, Thermococcus literolis,* a *Thermotoga* species, or a recombinant form thereof.

"Thermal cycle" includes any change in the incubation temperature of a nucleic acid sample designed to change the activity of a component of the sample such as, e.g., the binding affinity of a primer for a nucleic acid.

The terms "hybridize" or "hybridization" are art-recognized and include the hydrogen bonding of complementary DNA and/or RNA sequences to form a duplex molecule. Typically, hybridization takes place between a primer and template but may also take place between primers and these reactions, when undesired or unscheduled, can be inhibited by using methods and compositions of the invention.

The terms "amplification" or "amplify" include the reactions necessary to increase the number of copies of a nucleic acid sequence, such as a DNA sequence. For the purposes of the present disclosure, amplification refers to the in vitro exponential increase in copy number of a target nucleic acid sequence, such as that mediated by a polymerase amplification reaction such as the PCR. Other amplification reactions encompassed by the invention include RT-PCR (see, e.g., U.S. Pat. No. 4,683,202; Mullis et al.), and the ligase chain reaction (Barany, *Proc. Natl. Acad. Sci. USA* 88:189-193 (1991)).

"Selective amplification" refers to the preferential copying of a target or template nucleic acid of interest using a polymerase amplification reaction, such as the PCR.

The practice of the invention will employ, unless otherwise indicated, conventional techniques of molecular biology, microbiology and recombinant DNA techniques, which are within the skill of those in the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.).

Figure 4:
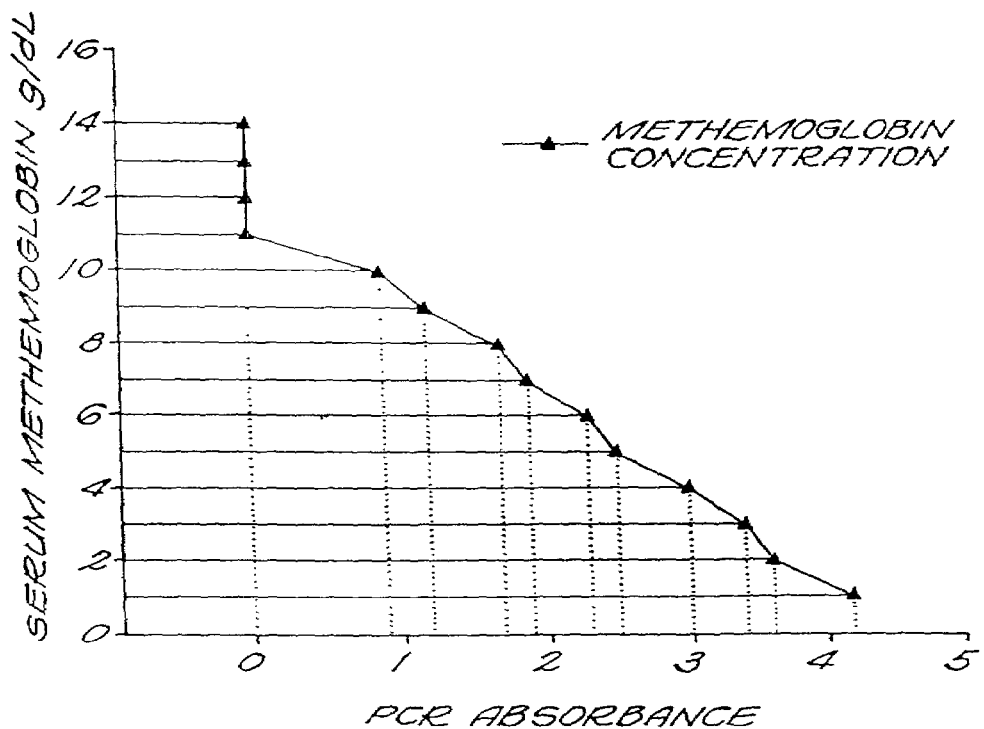
FIG. 4 is a graph showing the interference of methemoglobin on PCR absorbance in a PCR amplification assay on hepatitis B sequences MD03/06 in untreated serum.
Figure 5:
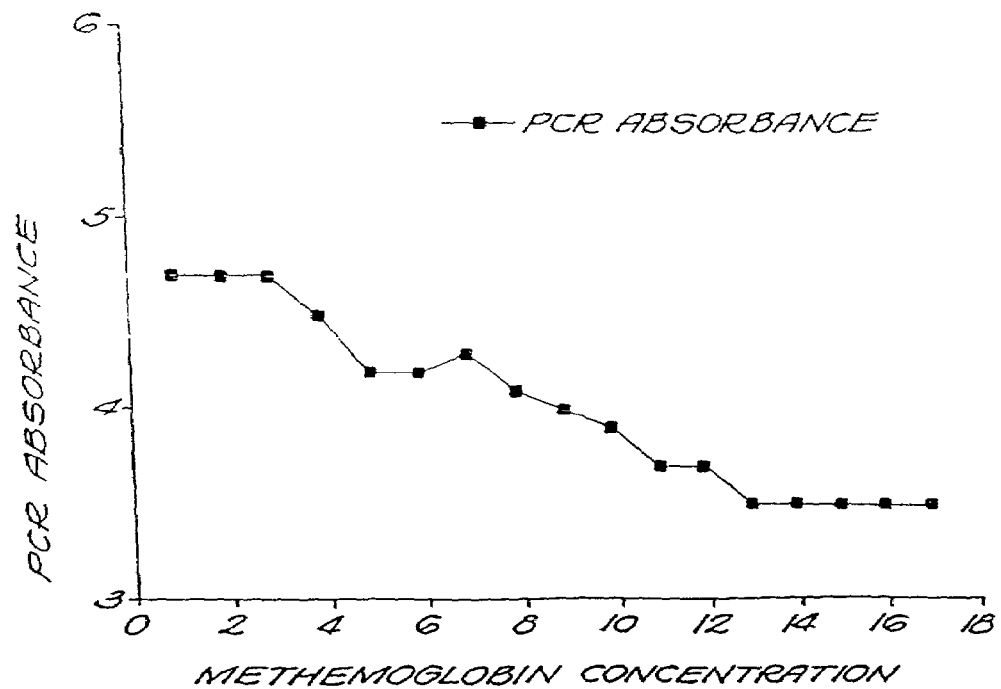
FIG. 5 is a graph showing the improvement in attenuating the interference of methemoglobin on PCR absorbance in a PCR amplification assay on hepatitis B sequences MD03/06 in serum which has been treated with a preservative of the invention.

The reagents of the invention have surprisingly been found to remove the interference of masking agents, e.g., heme proteins including methemoglobin on PCR assays run on blood serum. FIGS. 4 and 5 illustrate the improvement obtained by use of the reagents disclosed herein. Increasing amounts of methemoglobin were spiked into untreated fresh human serum, to a concentration of 10 dl/ml. Serial PCR assays were run over a four hour period.

Figure 6:
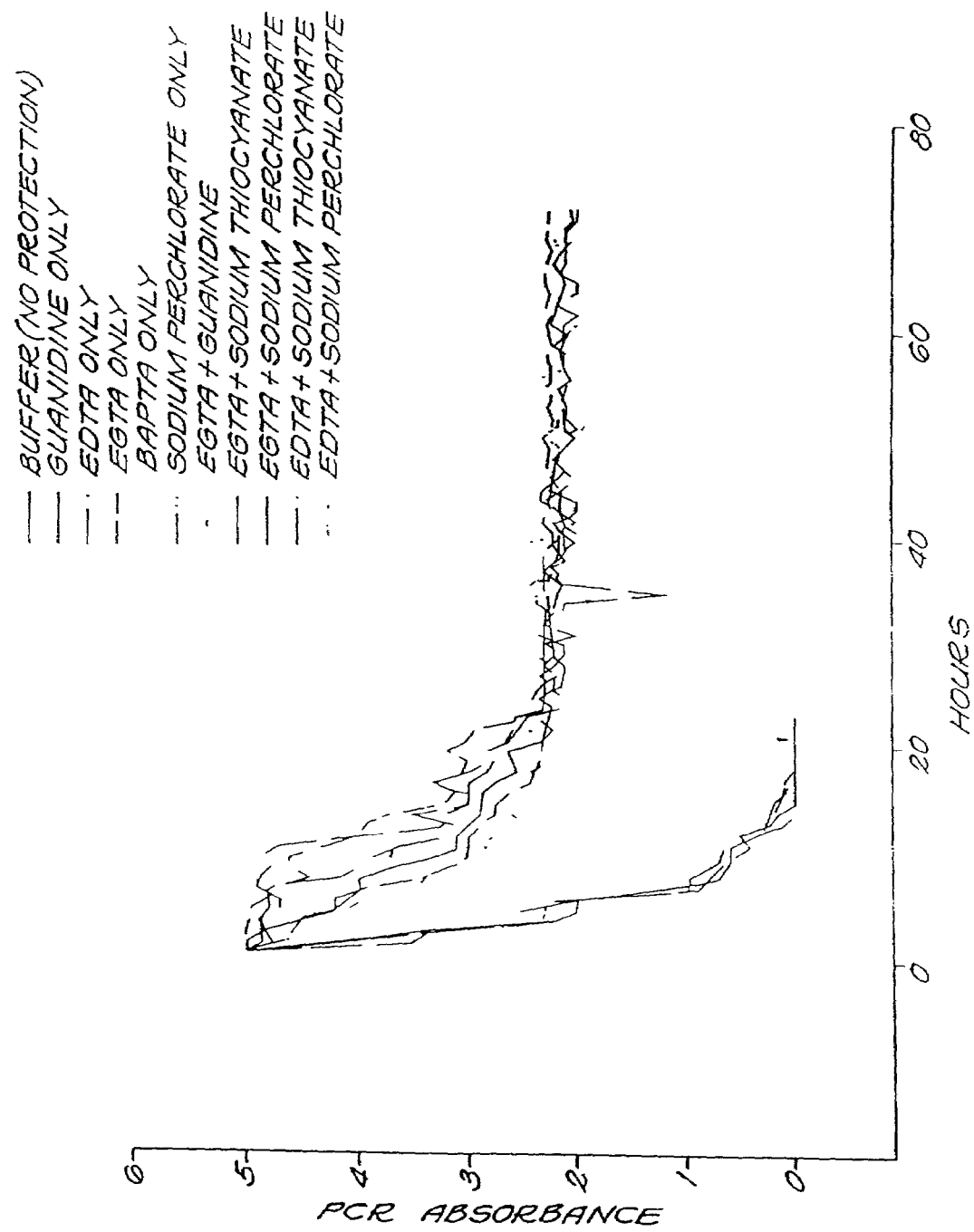
FIG. 6 illustrates the synergistic effect provided by the components of the inventive reagents in protecting hepatitis B sequences in serum stored at room temperature and subsequently subjected to MD03/06 PCR detection.

FIG. 6 illustrates the surprising and synergistic effect obtained by the combination of divalent metal chelators and chelator enhancing components in the inventive reagent (i.e., 1M sodium perchlorate/0.01M EGTA) in protecting hepatitis B sequences in serum stored at room temperature and subsequently subjected to MD03/06 PCR detection. The protocol run was as above (i.e., as illustrated in FIG. 6.) It can be seen from the figures that compared to the addition of EGTA or sodium perchlorate individually, protection of Hep B sequences is dramatically increased when reagent solutions of the present invention are used.

In an advantageous embodiment, the invention also enables the molecular assay of nucleic acids in other bodily fluids and excretions to be carried out with greater sensitivity, as the methods and reagents of the invention have been found to surprisingly increase the signal obtained with such molecular assays as the PCR. Additionally, hybridization in such nucleic acid testing methods is unexpectedly improved.

The methods and preservatives of the invention may further include an amount of at least one enzyme inactivating component such as manganese chloride, sarkosyl, or sodium dodecyl sulfate, generally in the range of about 0-5% molar concentration.

The reagents of the invention may be used advantageously to prokaryotic, e.g., gonococcal DNA, although the teachings of the invention may be readily applied to the preservation of other types of DNA, including human, bacterial, fungal, and viral DNA, as well as to RNA. The reagents of the invention are believed to function by inter alia, inactivating two classes of enzymes present in bodily fluids such as blood or urine which the inventor has recognized as destructive to DNA integrity, metal-dependent and metal independent enzymes.

Figure 7:
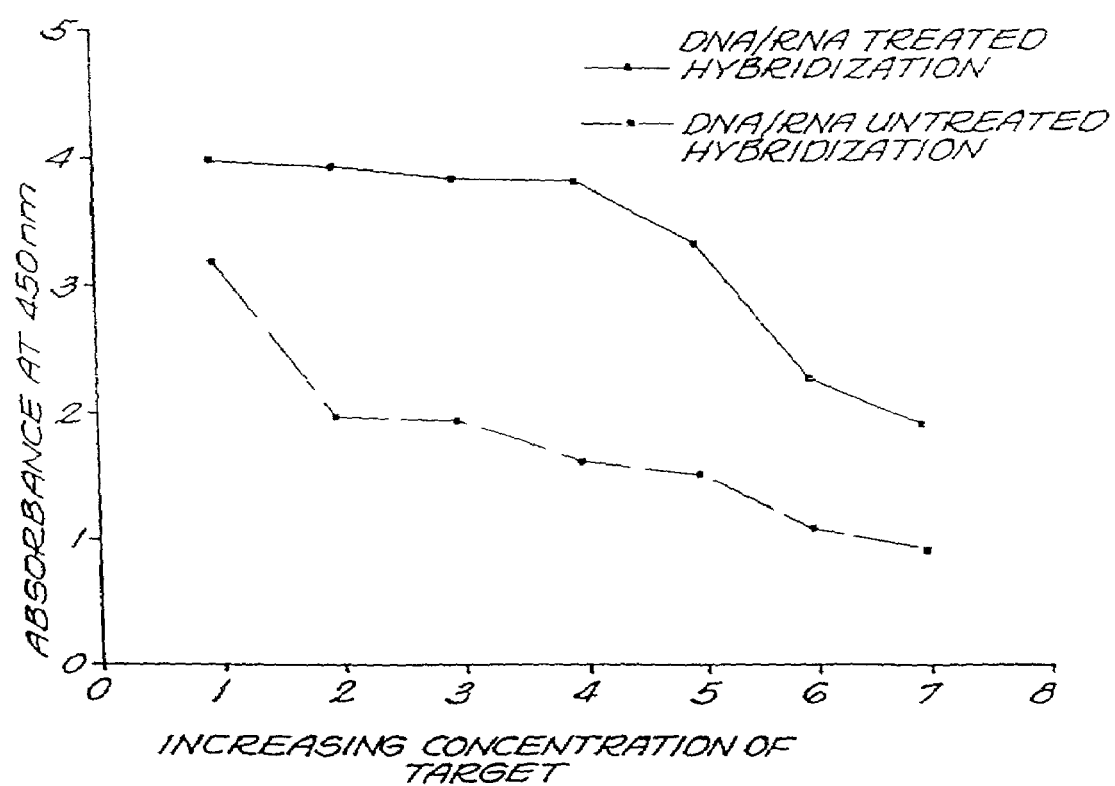
FIG. 7 graphically illustrates a comparison of signal response in PCR assays wherein the DNA has been treated with a reagent of the invention, and one which has not.
Figure 8:
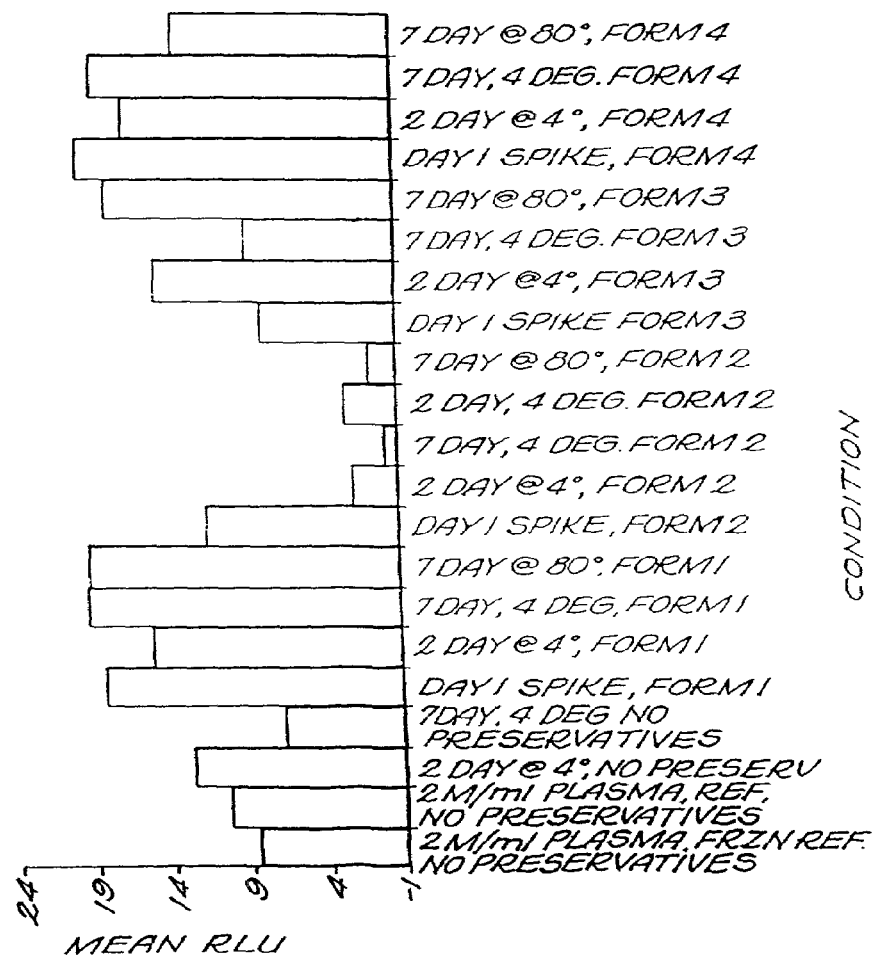
FIG. 8 illustrates the efficacy of reagents of the present invention to enhance signal response of a branched DNA assay of blood plasma samples subjected to various storage conditions.

The methods and reagents of the invention have been found to increase the signal obtained with such nucleic acid testing methods as the polymerase chain reaction (PCR), $LC_x$, and genetic transformation testing (GTT). The invention has been found to surprisingly and unexpectedly enhance hybridization in such nucleic acid testing methods as the PCR. FIGS. 7 and 8 illustrate the improvement in hybridization obtained by use of a reagent disclosed herein on the hybridization of penicillinase-producing *Neisseria gonorrhea* (PPNG) DNA and PPNG-C probe.

A further aspect of the invention relates to methods of improving hybridization of nucleic acids, including contacting a test nucleic acid with a nucleic acid reagent solution comprising an amount of a divalent metal chelator in the range of, e.g., about 0.001M to 0.1M; and an amount of at least one chelator enhancing component in the range of, e.g., about 0.1M to 2M, such that a test solution is formed; and contacting the test solution with a target nucleic acid under conditions favorable for hybridization, such that hybridization occurs.

Figure 9:
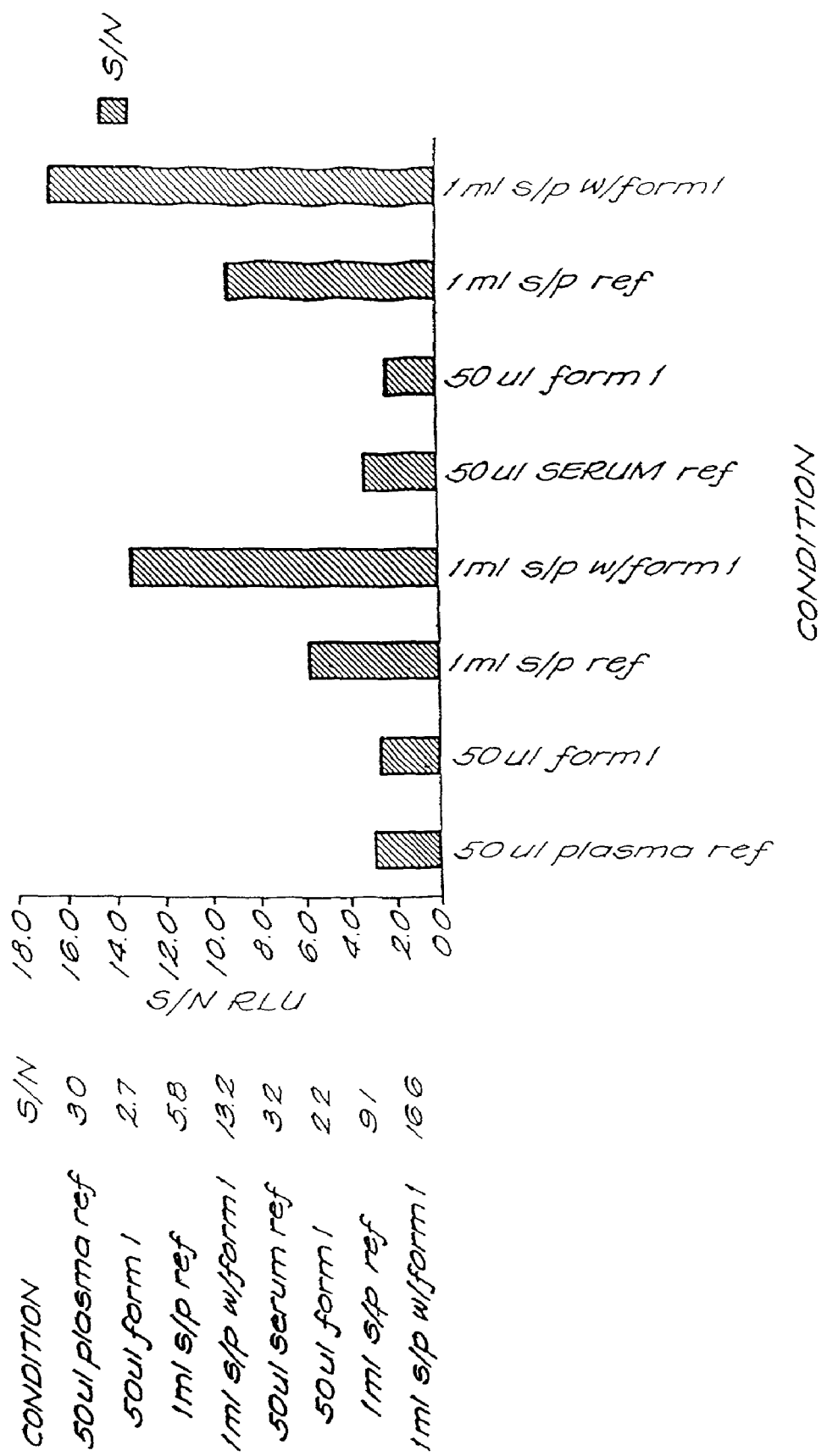
FIG. 9 illustrates the efficacy of reagents of the present invention to enhance signal response of a branched DNA assay of blood serum and plasma samples.

FIGS. 8 and 9 illustrate the efficacy of the methods and reagents of the invention in improving the results obtained with nucleic acid testing methods, in this case, a branched DNA assay (Chiron). In the tests run in FIG. 8, the bDNA assay was used to assess the effect of the reagents of the invention. DNA sequences from the hepatitis C virus were spiked into serum and plasma. The treated serum and plasma were mixed with 9 ml of serum or plasma and 1 ml of reagent. The following formulations were used: 1) 1M guanidine HCl/0.01M EDTA, 2) 1M sodium perchlorate/0.01M BAPTA, 3) 1M sodium thiocyanate/0.01M EGTA, and 4) 1M lithium chloride/0.01M EGTA. The formulations were stored for seven days at 4° C. bDNA assay relies on hybridization; it can clearly be seen from the absorbance results that the more than doubling of the absorbance results indicates an enhancement of hybridization/annealing of the target sequences.

FIG. 9 illustrates a serum v. plasma study. 50 ml samples of fresh human plasma, and 1 ml samples of fresh human serum were treated with 1M guanidine HCL/0.01M EDTA and the bDNA assay was run on these samples after the samples were stored at 20° F. for 48 hours. Results were compared to untreated samples. It can clearly be seen from the absorbance results that the more than doubling of the absorbance results indicates an enhancement of hybridization/annealing of the target sequences.

The invention has the advantage of being conveniently incorporated into established protocols without the need for extensive re-optimization.

In a preferred method, the PCR process is carried out as an automated process utilizing a thermostable enzyme. The reaction mixture is cycled through a denaturing step, a probe and primer annealing step, and a synthesis step, whereby cleavage and displacement occurs simultaneously with primer-dependent template extension. A DNA thermal cycler, which is specifically designed for use with a thermostable enzyme, may be employed.

Detection or verification of the labeled oligonucleotide fragments may be accomplished by a variety of methods and may be dependent on the source of the label or labels employed. One convenient embodiment of the invention is to subject the reaction products, including the cleaved labeled fragments, to size analysis. Methods for determining the size of the labeled nucleic acid fragments are known in the art, and include, for example, gel electrophoresis, sedimentation in gradients, gel exclusion chromatography and homochromatography.

During or after amplification, separation of the labeled fragments from the PCR mixture can be accomplished by, for example, contacting the PCR mixture with a solid phase extractant (SPE). For example, materials having an ability to bind oligonucleotides on the basis of size, charge, or interaction with the oligonucleotide bases can be added to the PCR mixture, under conditions where labeled, uncleaved oligonucleotides are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1000, Selectacel™ PEI, Boronate SPE with a 3'-ribose probe, SPE containing sequences complementary to the 3'-end of the probe, and hydroxylapatite. In a specific embodiment, if a dual labeled oligonucleotide comprising a 3' biotin label separated from a 5' label by a nuclease susceptible cleavage site is employed as the signal means, the PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step in which the PCR mixture has been contacted with an SPE, the SPE material can be removed by filtration, sedimentation, or magnetic attraction, leaving the labeled fragments free of uncleaved labeled oligonucleotides and available for detection.

For detecting the resultant PCR product, any art recognized technique may be used, such as agarose gel electrophoresis, as described herein. Alternatively, the resultant products of the amplification reaction may be detected using a detectable label, that is, e.g., isotopic, fluorescent, calorimetric, or detectable e.g., using antibodies. Accordingly, the amplification methods of the invention may be advantageously used to amplify virtually any target nucleic acid such as a nucleic acid fragment, gene fragment (e.g., an exon or intron fragment), cDNA, or chromosomal fragment.

Genotyping by SNP (single nucleotide polymorphism) analysis and allele-specific oligonucleotide (ASO) hybridizations, which are the basis for microarray or DNA-Chip methods, are other genomic methods that are expected to benefit from a technology for enhanced accuracy of hybridization. Microarrays are constructed by arraying and linking PCR amplified cDNA clones or genes to a derivatized glass plate. Currently, the linking chemistries depend on high-salt buffers with formamide or dimethyl sulfoxide (DMSO) to denature the DNA and provide more single-stranded targets for eventual hybridization with high specificity and minimal background. This is a critical step in the preparation of reproducible, high-fidelity microarrays which may benefit from reversibly modified nucleic acids developed in this project. Further, the specific conditions of the pre-hybridization and hybridization steps can dramatically affect the signal from the microarray and technology from this project may be able to improve microarray performance at this step of the process.

Diagnostic Applications

The methods, compositions, and kits of the invention are useful in a variety of diagnostic applications, such as the amplification and detection of nucleic acid sequences found in genomic DNA, bacterial DNA, fungal DNA, or viral RNA or DNA. The invention may also be used to detect or characterize nucleic acid sequences associated with infectious diseases (e.g., gonorrhea, chlamydia), genetic disorders, or cellular disorders such as cancer; or for the detection of certain types of non-genetic diseases (e.g., to detect the presence of a viral nucleic acid molecule (e.g., HIV or hepatitis) within a nucleic acid sample derived from a human cell sample). Surface analysis, e.g., through the use of microarrays or gene chips, to detect the possible presence of, e.g., biowarfare agents, can be aided through the practice of the present invention.

Forensic Applications

Forensic science is concerned with the scientific analysis of evidence from a crime. Forensic biology applies the experimental techniques of molecular biology, biochemistry, and genetics to the examination of biological evidence for the purpose, for example, of positively identifying the perpetrator of a crime. Typically, the sample size of such biological evidence (e.g. hair, skin, blood, saliva, or semen) is very small and often contains contaminants and interferents of molecular assays. Accordingly, the techniques of the invention may be advantageously used to detect, e.g., the sex or species of origin of even minute biological samples.

Research Applications

The methods and compositions of the invention have a variety of research applications. For example, they are useful for any research application in which genetic analyses must be performed on limited amounts of nucleic acid sample.

In general, the practice of the present invention employs, unless otherwise indicated, conventional techniques of chemistry, molecular biology, recombinant DNA technology, PCR technology, immunology, and any necessary cell culture or animal husbandry techniques, which are within the skill of the art and are explained fully in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Quantitative PCR Protocols*, Kochanowski et al., Eds., Humana Press (1999); *Clinical Applications of PCR*, Lo, Ed., Humana Press (1998); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990); and *Manipulating the Mouse Embryo*, Hogan et al., C.S.H.L. Press, Pub (1994).

The following exemplification is included for purposes of illustration and should not be construed as limiting the invention.

EXAMPLE 1

PCR Detection of Penicillinase-producing *Neisseria Gonorrhea*

The PCR signal-enhancing effect of the reagents of the invention is demonstrated by the following example. Four varieties of TEM-encoding plasmids are found in PPNG. These are the 6.7 kb (4.4 Mda) Asian type, the 5.1 kb (3.2 Mda) African type, the 4.9 kb (3.05-Mda) Toronto type and the 4.8 kb (2.9-Mda) Rio Type. This PCR assay for PPNG takes advantage of the fact that the TEM-1 gene is located close to the end of the transposon Tn2; by the use of one primer in the TEM-1 gene and the other in a sequence beyond the end of Tn2, and common to all four plasmids, a PCR product only from plasmids and not from TEM-1 encoding plasmids was obtained. (Table 1, below) The conditions associated with this protocol were modified to include the reagent of the invention in the hybridization and the treated probe was mixed with the 761-bp amplification product per standard PCR protocol. The results were read at $A_{450\,nm}$.

Materials and Reagents:
  BBL chocolate II agar plates
  Sterile Tris Buffer 10 mM Tris (pH 7.4), 1 mM EDTA
  0.5-ml Gene Amp reaction tubes
  Sterile disposable Pasteur pipette tips
  Aerosol-resistant tips
  PCR master mix:
    50 mM KCL
    2 mM MgCl
    50 µM each of
      Deoxyribonucleoside triphosphate;
      2.5 U of Taq Polymerase (Perkin Elmer);
      5% glycerol;
      50 pmol each of primers PPNG-L and PNG-R (per 100 µl reaction)
  Denaturation solution
    1M Na 5× Denhardt's solution
  Prehybridization Solution
    5×SSC(1×SSc is 0.015 M NaCl plus 0.015 M sodium citrate);
    5× Denhardt's solution;
    0.05% SDS;
    0.1% Sodium Ppi, and
    100 µg of sonicated salmon sperm DNA per ml.
  Hybridization Solution
    Same as prehybridization solution but without Denhardt's solution and including 200 µo of a reagent of the invention.
  1 ml of a reagent of the invention (1M guanidine HCl/ 0.01M EDTA, "Reagent 1")
  Avidin-HRP peroxidase complex (Zymed)
  Magnetic microparticles (Seradyne)

TABLE 1

| Function | Name | Nucleotide sequence 5' to 3' |
|---|---|---|
| Primer | PPNG-L | AGT TAT CTA CAC GAC GC (SEQ ID NO: 1) |
| Primer | PPNG-R | GGC GTA CTA TTC ACT CT (SEQ ID NO: 2) |
| Probe | PPNG-C | GCG TCA GAC CCC TAT CTA TAA ACT C (SEQ ID NO: 3) |

TABLE 1-continued

Methods:
Sample preparation: 2 colonies were picked from a chocolate agar plate. Colonies were suspended in DI water just prior to setting up PCR. The master mix was prepared according to the recipe above. 5µl of the freshly prepared bacterial suspension was added to 95 µl of master mix. The DNA was liberated and denatured in a thermocycler using three cycles of 3 min at 94° C. and 3 min at 55°. The DNA was amplified in the thermal cycler by using a two step profile: a 25s denaturation at 95° C. and a 25s annealing at 55° C. for a total of thirty cycles. The time was set between the two temperature plateaus to enable the fastest possible annealing between the two temperatures. 15 pmol of labeled (avidin-HRP complex) detection probe PPNG-C was added to the hybridization solution bound to magnetic micro particles with and without the preservative reagent at 37° C. for 1 hour. The control and treated probes were then added to the amplification product and the reaction was calorimetrically detected at $A_{450\,nm}$. The signal obtained from the hybridization probes treated with a reagent of the invention was found to be significantly higher than the untreated probes.

EXAMPLE 2

Inhibition of amplification is a significant problem with STD specimens from both cervical and urethral sites. Based on a review of the literature, estimates of inhibition range from 2-20% for specimens collected with a swab. This experiment compares a novel swab collection device containing a reagent of the invention to a standard dry swab collection device and demonstrates that reagents of the invention can be utilized to significantly minimize the effects of inhibition, thereby reducing the incidence of false negative results.

The swab device used was a sterile polyurethane sponge impregnated with 700 µl of the reagent of Example 1, which is housed in the bottom of an empty sterile tube. The specimen is collected on a separate sterile rayon swab and inserted into the above tube (Starplex). Once the swab has been inserted in the tube, the swab comes into contact with the sponge and absorbs the reagent, which treats the specimen accordingly. The control device used for comparison was a standard dry rayon swab in a sterile tube (Copan Diagnostics #155 C-160 C).

Four known amplification assays were included in this study: LCx® (Abbott Diagnostics), Probe-Tec® (BD Diagnostic Systems), TMA™ (Gen-Probe), and PCR® (Roche Diagnostics). Four separate laboratories were utilized to conduct the experiment, one for each assay platform.

Specimens were collected at four separate STD clinics using best-practice collection methods. At each collection site, 50 patients provided duplicate specimens for an aggregate of 200 treated samples and 200 untreated samples. All samples were transported to the laboratory at room temperature and processed within 8 hours of collection.

Current assay reagents and direction inserts were used to perform the amplification assay. A second amplified assay was utilized to challenge all positives to confirm that they were really true positives. LCx was refereed by PCR, and SDA, TMA, and PCR were all refereed by LCx. Additionally, all positive extracts that were untreated (dry) were subjected to GC/MS analysis to confirm the presence of substances known to cause inhibition in amplified assay systems. Target substances were leukocyte esterase, methemoglobin, lactoferrin, hydrogen peroxide, and lactic acid. Furthermore, immunoassays were preformed to detect the presence of the following inhibitors:
   Gamma interferon
   Mucosal IgA
   Non-target bacterial DNA Data:

1) Comparison Between True Positives Using Reagent 1 and an Untreated Control
   Number of collection sites: 4
   Collection site 1: Cervical Chlamydia (asymptomatic)
   Collection site 2: Urethral Gonorrhea (symptomatic)
   Collection site 3: Cervical Chlamydia(asymptomatic)
   Collection site 4: Urethral Gonorrhea (symptomatic)
   Number of Samples that were Treated: 200 (50 from each collection site).
   Number of Samples that were untreated: 200 (50 from each collection site).

| Test Site #/ Assay | Number of Samples | Positives- (Treated w/Reagent 1) | Prevalence | Number of Samples | Positives- Untreated control | Prevalence |
|---|---|---|---|---|---|---|
| 1 - LCx | 50 | 8 | 16% | 50 | 6 | 12% |
| 2 - Probe-Tec | 50 | 7 | 14% | 50 | 4 | 8% |
| 3 - TMA | 50 | 5 | 10% | 50 | 3 | 6% |
| 4 - PCR | 50 | 6 | 12% | 50 | 3 | 6% |
| Totals: | 200 | 26 | 13% | 200 | 16 | 8% |

2) GC/MS Cervical Data for Untreated Inhibited Specimens:
   Lactoferrin>175 g/mg
   Methemoglobin>8 mg/dl
   Leukocyte esterase>15/μL
   Lactic Acid: present, but not quantified
   *All had statistically significant correlation with inhibited specimens 3) GC/MS Urethral Data for Untreated Inhibited Specimens:
   Neutrophil Esterase>15 μl (achieved peaks)
   Hydrogen peroxide: present, but not quantified
   Zinc 110 μg/dl

*All had statistically significant correlation with inhibited specimens

4) Immunoassay Data for Untreated Inhibited Specimens:
   IgA cervical correlation
   Gamma Interferon urethral and cervical correlation
   Protein oxidation (hydroxy-nonenal) activity urethral correlation only Results 1) Swabs impregnated with Reagent 1 yielded a statistically significant increase in amplification at all sites compared to a standard untreated swab.
2) There was no statistically significant difference between gonorrhea and chlamydia specimens with regard to their inhibition characteristics.
3) There was a statistically significant presence of target inhibitors in both untreated gonorrhea and chlamydia specimens.
4) Lactoferrin, hydrogen peroxide, methemoglobin, gamma interferon, lactic acid, leukocyte esterase were all associated with inhibited specimens.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of suppressing the interference of a masking agent selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulfhemoglobin, and bilirubin, on a molecular assay of a nucleic acid-containing bodily fluid, the method comprising:

contacting the bodily fluid with a reagent consisting of from about 0.01 M to about 0.1 M of a divalent metal chelator and from about 0.1 M to 1.0 M of a chelator enhancing component selected from the group consisting of lithium chloride, sodium salicyl ate, and combinations thereof;

wherein the interference of the masking agent on the molecular assay of the nucleic acid-containing bodily fluid is suppressed.

2. A method according to claim 1, wherein the divalent metal chelator is selected from the group consisting of ethylenediaminetetraacetic acid, imidazole, ethylenebis(oxyethylenenitriol)tetraacetic acid; iminodiacetate; and 1,2-bis(2-aminophenoxy)ethane-N,N,N',N'-tetraacetic acid; bis(5-amidino-2-benzimidazolyl)methane and salts thereof.

3. A method of suppressing the interference of a masking agent selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulfhemoglobin, and bilirubin, on a molecular assay of a nucleic acid-containing bodily fluid, the method comprising:

contacting the bodily fluid with a reagent having from about 0.01 M to about 0.1 M of a divalent metal chelator and from about 0.1 M to 1.0 M of a chelator enhancing component selected from the group consisting of lithium chloride, sodium salicylate, sodium perchlorate, sodium thiocyanate, and combinations thereof, wherein the interference of the masking agent on the molecular assay of the nucleic acid-containing bodily fluid is suppressed.

4. A method according to claim 3, wherein the divalent metal chelator is selected from the group consisting of ethylenediaminetetraacetic acid, imidazole, ethylenebis(oxyethylenenitriol)tetraacetic acid; iminodiacetate; and 1,2-bis(2-aminophenoxy)ethane-N,N,N',N'-tetraacetic acid; bis(5-amidino-2-benzimidazolyl)methane and salts thereof.

5. A method according to claim 3, wherein the divalent metal chelator is selected from the group consisting of ethylenediaminetetraacetic acid and 1,2-bis(2-aminophenoxy)ethane-N,N,N',N'-tetraacetic acid, and salts thereof.

6. A method decording to claim 3, wherein the masking agent is selected from the group consisting of a leukocyte esterase and a heme protein.

7. A method according to claim 3, wherein the heme protein is selected from the group consisting of a myoglobin analogue, a hemoglobin analogue, a myoglobin oxidation product, a hemoglobin oxidation product, a myoglobin breakdown product, and a hemoglobin breakdown product.

8. A method according to claim 3, wherein the masking agent is selected from the group consisting of a ferritin, methemoglobin, sulthemoglobin and bilirubin.

9. A method according to claim 3, wherein the masking agent is selected from the group consisting of methemoglobin and bilirubin.

10. A method according to claim 3, wherein the nucleic acid is selected from the group consisting of DNA, RNA, mRNA, and cDNA.

11. A method according to claim 3, wherein the nucleic acid is eukaryotic DNA.

12. A method according to claim 3, wherein the molecular assay is selected from the group consisting of a polymerase chain reaction, a ligase chain reaction, nucleic acid sequence-based amplification, strand displacement amplification, and a genetic transformation test.

13. A method according to claim 3, wherein the molecular assay comprises a polymerase chain reaction.

14. A method of improving the signal response of a molecular assay of a nucleic acid-containing bodily fluid the method comprising:

contacting the nucleic acid-containing bodily fluid with a reagent consisting of from about 0.01 M to about 0.1 M of a divalent metal chelator and from about 0.1 M to 1.0 M of a chelator enhancing component selected from the group consisting of lithium chloride, sodium salicylate, and combinations thereof to form a preserved test sample, wherein the interference of a masking agent selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulfhemoglobin, and bilirubin on the molecular assay is suppressed;

extracting molecular analytes of interest from the preserved test sample; and conducting a molecular assay on the extracted molecular analytes of interest, wherein the signal response of the molecular assay is improved relative to a molecular assay performed without the reagent.

15. A method according to claim 14, wherein the divalent metal chelator is selected from the group consisting of ethylenediaminetetraacetic acid, imidazole, ethylenebis(oxyethylenenitriol)tetraacetic acid; iminodiacetate; and 1,2-bis(2-aminophenoxy)ethane-N,N,N',N'-tetraacetic acid; bis(5-amidino-2-benzimidazolyl)methane and salts thereof.

16. A method of improving the signal response of a molecular assay of a nucleic acid-containing bodily fluid, the method comprising:

contacting the nucleic acid-containing bodily fluid with a reagent having from about 0.01 M to about 0.1 M of a divalent metal chelator and from about 0.1 M to 1.0 M of a chelator enhancing component selected from the group consisting of lithium chloride, sodium salicylate, sodium perchlorate, sodium thiocyanate, and combinations thereof to form a preserved test sample, wherein the interference of a masking agent selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulthemoglobin, and bilirubin on the molecular assay is suppressed;

extracting molecular analytes of interest from the preserved test sample; and conducting a molecular assay on the extracted molecular analytes of interest, wherein the signal response of the molecular assay is improved relative to a molecular assay performed without the reagent.

17. A method according to claim 16, wherein the divalent metal chelator is selected from the group consisting of ethylenediaminetetraacetic acid, imidazole, ethylenebis(oxyethylenenitriol)tetraacetic acid; iminodiacetate; and 1,2-bis(2-aminophenoxy)ethane-N,N,N',N'-tetraacetic acid; bis(5-amidino-2-benzimidazolyl)methane and salts thereof.

18. A method according to claim 16, wherein the divalent metal chelator is selected from the group consisting of ethylenediaminetetraacetic acid and 1,2-bis(2-aminophenoxy)ethane-N,N,N',N'-tetraacetic acid, and salts thereof.

19. A method according to claim 16, wherein the masking agent is selected from the group consisting of a leukocyte esterase and a heme protein.

20. A method according to claim 19, wherein the heme protein is selected from the group consisting of a myoglobin analogue, a hemoglobin analogue, a myoglobin oxidation product, a hemoglobin oxidation product, a myoglobin breakdown product, and a hemoglobin breakdown product.

21. A method according to claim 16, wherein the masking agent is selected from the group consisting of a ferritin, methemoglobin, sulihemoglobin and bilirubin.

22. A method according to claim 16, wherein the masking agent is selected from the group consisting of methemoglobin and bilirubin.

23. A method according to claim 16, wherein the bodily fluid is selected from the group consisting of urine, blood, blood serum, amniotic fluid; ccrcbrospinal and spinal fluid; synovial fluid; conjunctival fluid; salivary fluid; vaginal fluid; stool; seminal fluid; lymph; bile; tears, and sweat.

24. A method according to claim 23, wherein the bodily fluid is urine.

25. A method according to claim 16, wherein the nucleic acid is selected from the group consisting of DNA, RNA, mRNA, and cDNA.

26. A method according to claim 16, wherein the nucleic acid is cukaryotic DNA.

27. A method according to claim 16, wherein the molecular assay is selected from the group consisting of a polymerase chain reaction, a ligase chain reaction, nucleic acid sequence-based amplification, strand displacement amplification, and a genetic transformation test.

28. A method according to claim 16, wherein the molecular assay comprises a polymerase chain reaction.

29. A method of suppressing the interference of a masking agent selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulfhemoglobin, and bilirubin, on a molecular assay of a nucleic acid-containing bodily fluid, the method comprising:

contacting the bodily fluid with a reagent consisting of from about 0.01 M to about 0.1 M of a chelator selected from the group consisting of ethylenediaminetetraacetic acid, imidazole, ethylenebis(oxyethylenenitriol)tetraacetic acid; iminodiacetate; and 1,2-bis(2 aminophenoxy)ethane-N,N,N',N'-tetraacetic acid; bis(5-amidino-2-benzimidazolyl) methane and salts or combinations thereof, and from about 0.1 M to 1.0 M of a chelator enhancing component selected from the group consisting of lithium chloride, sodium salicylate, and combinations thereof;

thereby suppressing the interference of the masking agent on the molecular assay of the nucleic acid-containing bodily fluid.

30. A method of performing a molecular assay on a nucleic acid-containing bodily fluid, the method comprising:

suppressing the interference of a masking agent in the sample wherein the masking agent is selected from the group consisting of a leukocyte esterase, a heme protein, a myoglobin analogue, a hemoglobin analogue, a myoglobin derivative, a hemoglobin derivative, a myoglobin oxidation product, a hemoglobin oxidation product, a myoglobin breakdown product, a hemoglobin breakdown product, a ferritin, methemoglobin, sulffiemoglobin, and bilirubin, the suppressing comprising:

contacting the bodily fluid with a reagent consisting of from about 0.01 M to about 0.1 M of a chelator selected from the group consisting of ethylenediaminetetraacetic acid, imidazole, ethylenebis(oxyethylenenitriol)tetraacetic acid; iminodiacetate; and 1,2-bis(2 aminophenoxy)ethane-N,N,N',N'-tetraacetic acid; bis(5 -amidino-2-benzimidazolyl) methane and salts or combinations thereof, and from about 0.1 M to 1.0 M of a chelator enhancing component selected from the group consisting of lithium chloride, sodium salicylate, and combinations thereof; and performing the molecular assay on the bodily fluid wherein the masking agent is suppressed.

* * * * *